(12) United States Patent
Dudar

(10) Patent No.: US 10,436,138 B2
(45) Date of Patent: Oct. 8, 2019

(54) SYSTEMS AND METHODS FOR DIAGNOSING A VEHICLE ENGINE INTAKE MANIFOLD AND EXHAUST SYSTEM

(71) Applicant: Ford Global Technologies, LLC, Dearborn, MI (US)

(72) Inventor: Aed M. Dudar, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 106 days.

(21) Appl. No.: 15/657,655

(22) Filed: Jul. 24, 2017

(65) Prior Publication Data

US 2019/0024599 A1 Jan. 24, 2019

(51) Int. Cl.
| | |
|---|---|
| F02D 41/04 | (2006.01) |
| F02D 41/14 | (2006.01) |
| F01N 11/00 | (2006.01) |
| G01N 33/00 | (2006.01) |
| F02D 41/18 | (2006.01) |
| F02D 41/22 | (2006.01) |
| F02D 35/02 | (2006.01) |

(52) U.S. Cl.
CPC ......... *F02D 41/18* (2013.01); *F02D 41/1438* (2013.01); *F02D 41/1441* (2013.01); *F02D 41/182* (2013.01); *F02D 41/222* (2013.01); *G01N 33/0006* (2013.01); *F01N 2560/05* (2013.01); *F02D 35/02* (2013.01); *F02D 41/1445* (2013.01); *F02D 2041/223* (2013.01); *F02D 2200/0402* (2013.01)

(58) Field of Classification Search
CPC .. F02D 41/18; F02D 41/1438; F02D 41/1441; F02D 41/182; F02D 41/222; F02D 41/042; F02D 41/22; F02D 41/1445; F02D 35/02; F02D 2200/0402; F02D 2250/24; B60W 20/50; F01N 11/00; F01N 2550/00; F01N 2550/08
USPC ........................... 60/274, 277, 285, 286, 295
See application file for complete search history.

(56) References Cited

U.S. PATENT DOCUMENTS

| | | | |
|---|---|---|---|
| 6,895,934 B2 | 5/2005 | Kirschke et al. | |
| 7,562,561 B2 | 7/2009 | Murakami | |
| 8,224,559 B2 * | 7/2012 | Chang ................. | F02D 41/0087 123/479 |
| 8,239,088 B2 * | 8/2012 | Dingl .................... | F02D 41/221 701/29.1 |
| 8,424,288 B2 * | 4/2013 | De Tricaud ............ | F01N 3/103 60/278 |
| 9,347,417 B2 * | 5/2016 | Shomura ................. | F02N 19/00 |

(Continued)

*Primary Examiner* — Patrick D Maines
*Assistant Examiner* — Dapinder Singh
(74) *Attorney, Agent, or Firm* — Julia Voutyras; McCoy Russell LLP

(57) ABSTRACT

Methods and systems are provided for indicating a presence or absence of a source of degradation stemming from one of an intake manifold, exhaust system, or engine of an engine system. In one example, a method comprises rotating the engine unfueled and indicating the source of degradation based on both an intake air flow and an exhaust flow, as compared to baseline intake air flow and baseline exhaust flow. In this way, a source of degradation may be pinpointed, which may increase a lifetime of a vehicle engine system, reduce undesired emissions, and which may increase customer satisfaction resulting from shorter time spent on diagnosing such a source of degradation.

19 Claims, 8 Drawing Sheets

(56) References Cited

U.S. PATENT DOCUMENTS 9,714,030 B2 * 7/2017 Dudar .................. B60W 20/50
2003/0230287 A1 12/2003 Ozeki et al.
2009/0187301 A1 7/2009 Wang et al.

* cited by examiner

|  | Outcome from engine system diagnostic | Diagnosis |
|---|---|---|
| A | MAF ≈ baseline<br>GPF dP sensor > baseline | Degradation stemming from intake manifold |
| B | MAF ≈ baseline<br>GPF dP sensor < baseline | Degradation stemming from exhaust system |
| C | Both MAF and GPF dP sensor below baseline | Degradation stemming from engine and/or engine mechanical issues |
| D | MAF ≈ baseline<br>GPF dP sensor ≈ baseline | Absence of degradation stemming from intake manifold, engine, and exhaust system |

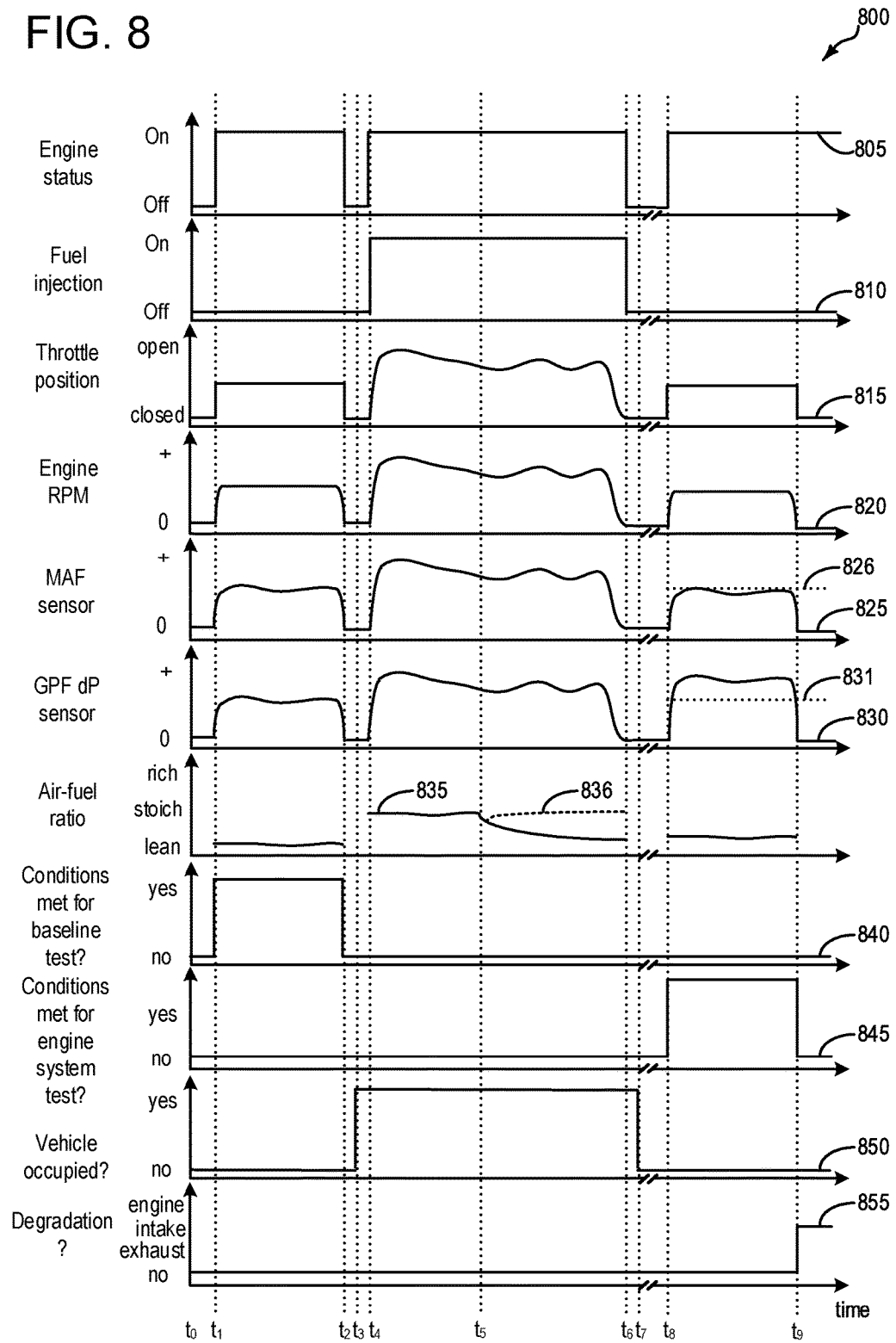

SYSTEMS AND METHODS FOR DIAGNOSING A VEHICLE ENGINE INTAKE MANIFOLD AND EXHAUST SYSTEM

FIELD

The present description relates generally to methods and systems for assessing the presence or absence of degradation in a vehicle engine, engine intake manifold, or engine exhaust system.

BACKGROUND/SUMMARY

Internal combustion engines combust a mixture of fuel and air in order to produce torque to propel a vehicle. Specifically, air is drawn into the engine via an engine intake manifold based on a position of a throttle, and then the air is mixed with fuel. The air-fuel mixture is combusted within engine cylinder(s), to drive piston(s) within the cylinder(s), thus rotating an engine crankshaft. By-products of combustion within the engine cylinders are routed to one or more catalysts via an exhaust manifold, prior to exiting to atmosphere.

Both the engine intake and exhaust systems may exhibit degradation, over time. Any presence of degradation in the intake system, exhaust system, or engine may lead to a decrease in fuel economy, and in some examples may lead to an increase in undesired emissions. The inventors have herein recognized these issues.

Engine operation may be regulated based on a number of parameters, such as the air flow rate provided to the engine. A measurement of air flow provided to the engine may be determined by a mass air flow (MAF) sensor, for example. However, in the intake manifold, any presence of degradation downstream of the MAF sensor may result in unmetered air being provided to the engine. As a result, the air-fuel ratio may switch lean. However, there are many other root causes for an engine running lean, such as undesired combustion, exhaust gas oxygen sensors that are not functioning as desired, valve timing issues, the MAF sensor not functioning as desired, etc. Thus, it can be challenging to specifically diagnose the presence or absence of degradation stemming from an intake system or intake manifold downstream of a MAF sensor. Similarly, degradation in the exhaust system may be difficult to pinpoint, if said degradation is downstream of an exhaust gas oxygen sensor, for example.

U.S. Patent No. US20090187301 teaches a method of diagnosing the presence or absence of degradation in an intake manifold of an engine, by comparing manifold absolute pressure to atmospheric pressure. In one example, a significant amount of degradation is indicated responsive to manifold absolute pressure being substantially equivalent to atmospheric pressure.

However, the inventors herein have recognized potential issues with such a method. For example, such a method is unable to diagnose the presence or absence of degradation in an exhaust system of the vehicle. Thus, the inventors have herein developed systems and methods to address such issues. In one example, a method is provided, comprising conducting an engine system diagnostic by rotating an engine of a vehicle unfueled to draw an intake air flow into the engine via an intake manifold and to route an exhaust flow via an exhaust system to atmosphere, and indicating a source of degradation stemming from one of the engine, the intake manifold, or the exhaust system based on both the intake air flow and the exhaust flow during the rotating. In this way, a robust determination of whether a source of degradation stems from either the intake manifold, the engine, or the exhaust system of the vehicle with one engine system diagnostic.

In one example, the method includes prior to conducting the diagnostic, obtaining a set of baseline comparator data that includes a baseline air intake flow and a baseline exhaust flow under a substantially equivalent set of conditions as that for conducting the engine system diagnostic, including rotating the engine unfueled via a motor powered by a battery. In such an example, the substantially equivalent set of conditions further comprises rotating the engine at a predetermined speed for a predetermined duration of time, and controlling a throttle positioned in the intake manifold to a predetermined position to allow air to be drawn into the engine via the intake manifold.

In some examples, the intake air flow and the baseline intake air flow may be measured via a mass air flow sensor positioned in the intake manifold, and where the exhaust flow and the baseline exhaust flow is measured via a pressure sensor positioned in the exhaust system. In such an example, the pressure sensor may comprise a differential pressure sensor corresponding to a gas particulate filter positioned in the exhaust system. Furthermore, obtaining the set of baseline comparator data may be conducted under conditions where the engine system is free from the source of degradation.

In one example, the source of degradation may be indicated in the intake manifold responsive to the intake air flow during the engine system diagnostic being substantially equivalent to the baseline intake flow, but where the exhaust flow during the engine system diagnostic is greater than the baseline exhaust flow.

In another example, the source of degradation may be indicated in the exhaust system responsive to the intake air flow during the engine system diagnostic being substantially equivalent to the baseline intake air flow, but wherein the exhaust flow is lower during the engine system diagnostic as compared to the baseline exhaust flow.

In another example, the source of degradation may be indicated as stemming from the engine responsive to both the intake air flow and the exhaust flow during the engine system diagnostic being lower than the baseline intake air being lower than the baseline intake air flow and the baseline exhaust flow, respectively.

In still another example, the source of degradation may not be present in any of the intake manifold, exhaust system, or engine responsive to both the intake air flow during the engine system diagnostic being substantially equivalent to the baseline intake air flow, and the exhaust flow during the engine system diagnostic being substantially equivalent to the baseline exhaust flow.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 7 shows an example lookup table that may be used to interpret results of the method of FIG. 5.

FIG. 8 shows an example timeline for determining whether degradation is present in a vehicle intake manifold, exhaust system, or engine, according to the methods of FIGS. 5-6.

DETAILED DESCRIPTION

Figure 2:
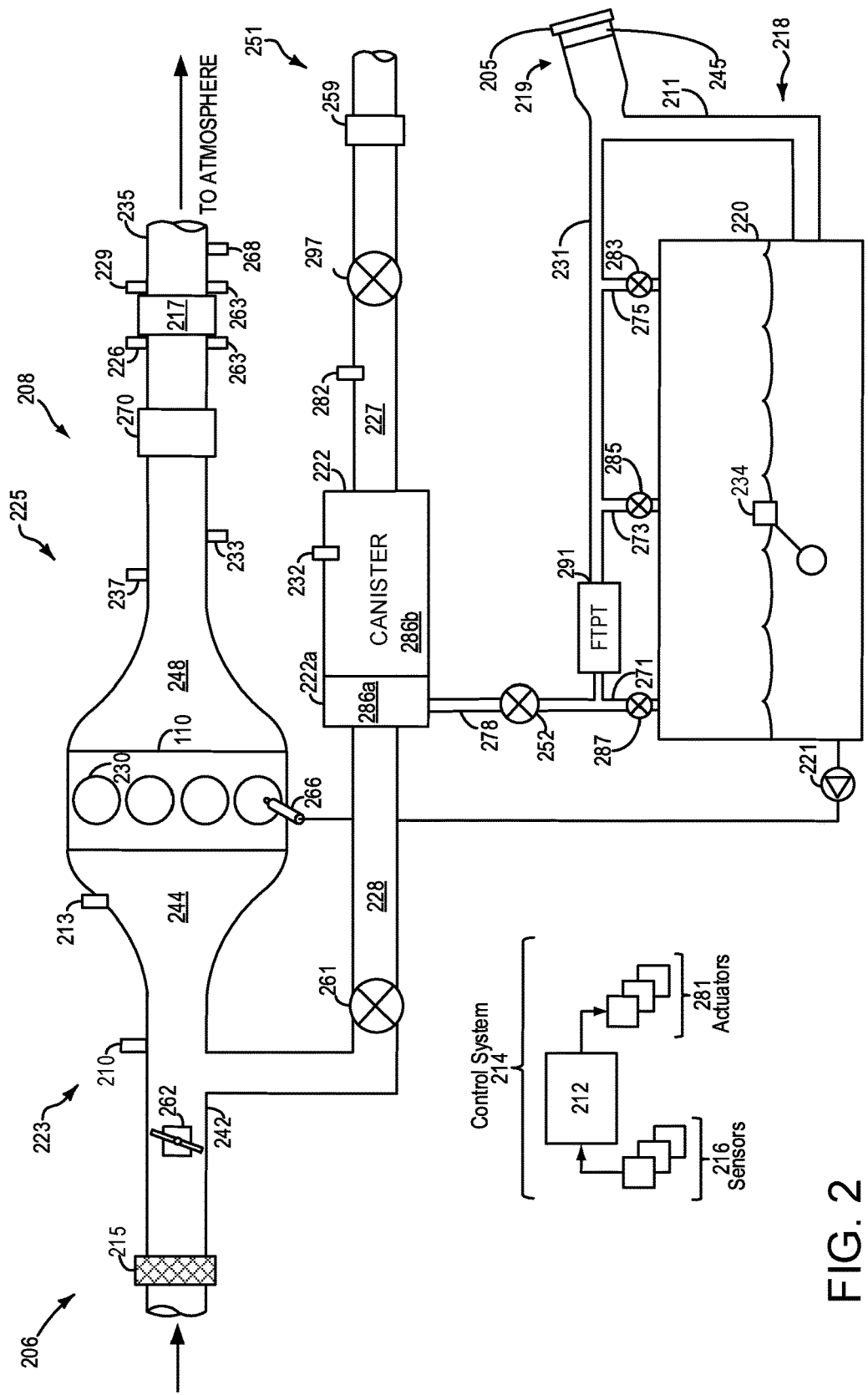
FIG. 2 schematically shows an example vehicle system with a fuel system and an evaporative emissions system.
Figure 3A:
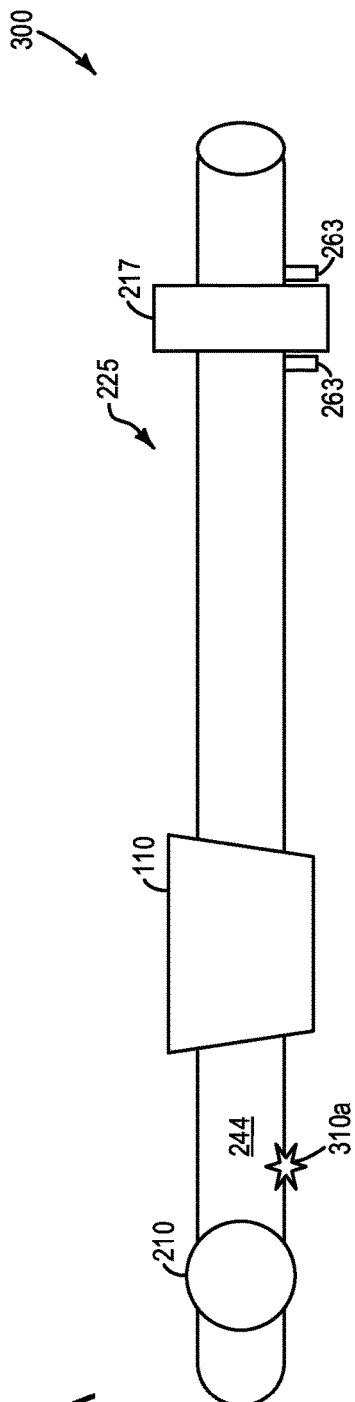
FIGS. 3A-3C schematically illustrates a block diagram of a vehicle intake and exhaust system of an engine, with potential locations for degradation illustrated.
Figure 3B:
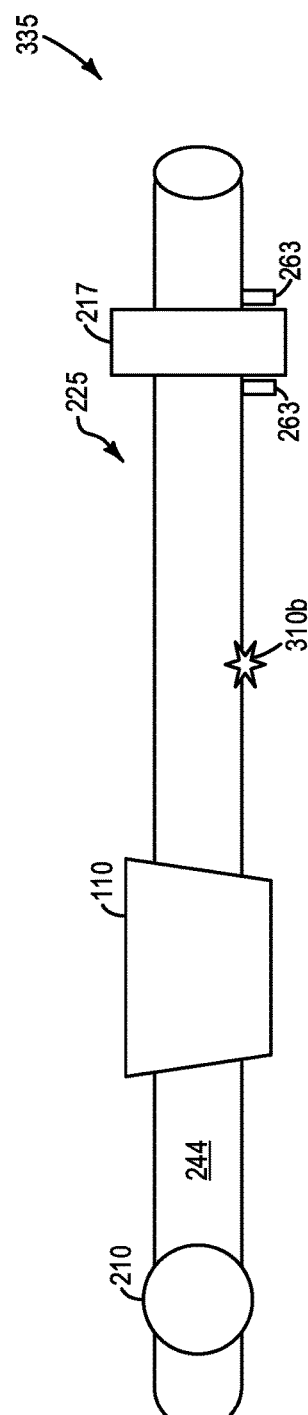
Figure 3C:
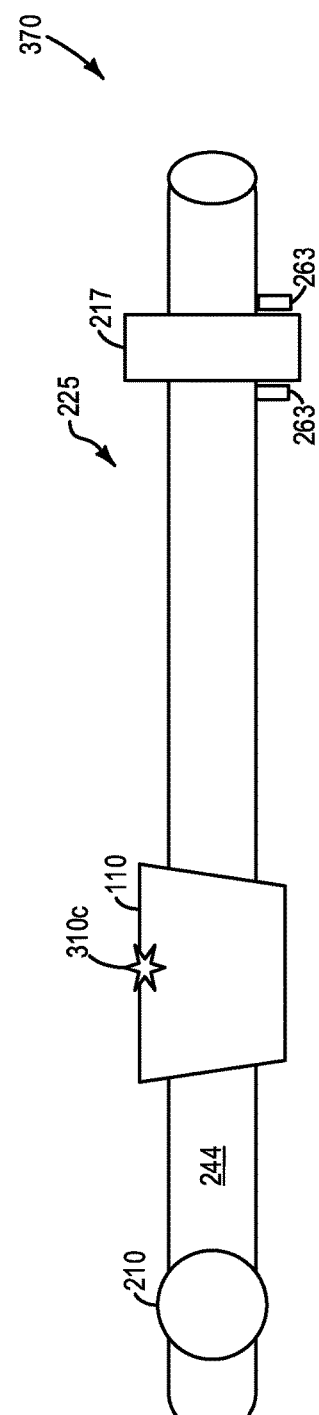
Figure 4:
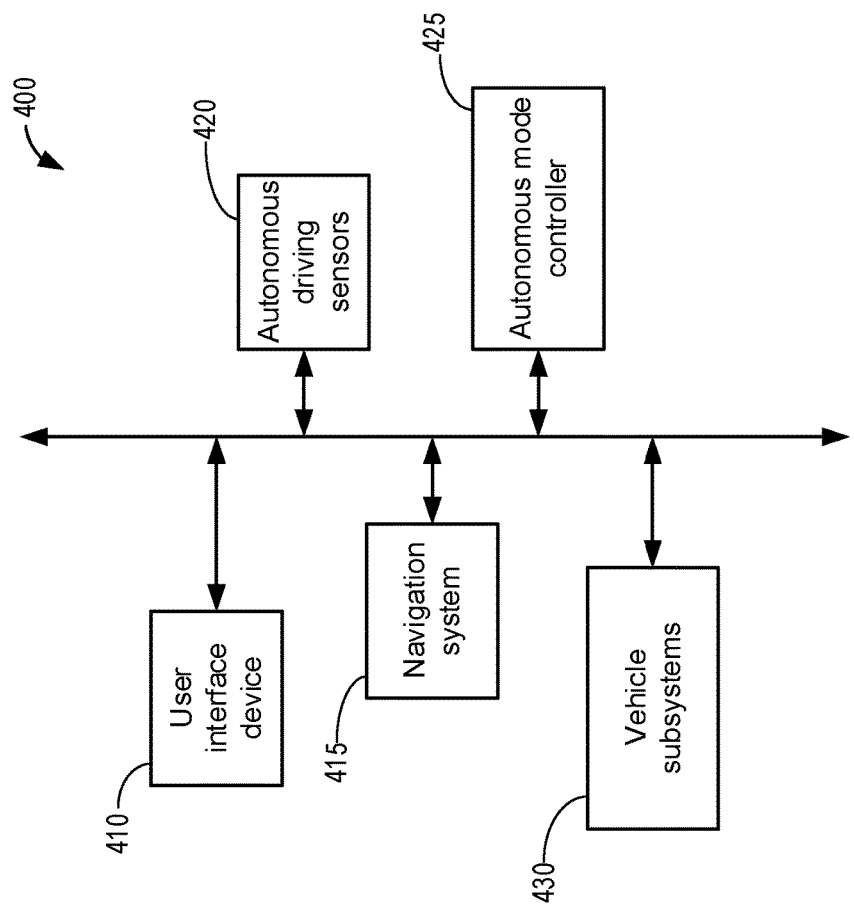
FIG. 4 schematically illustrates a block diagram of an example autonomous driving system.
Figure 5:
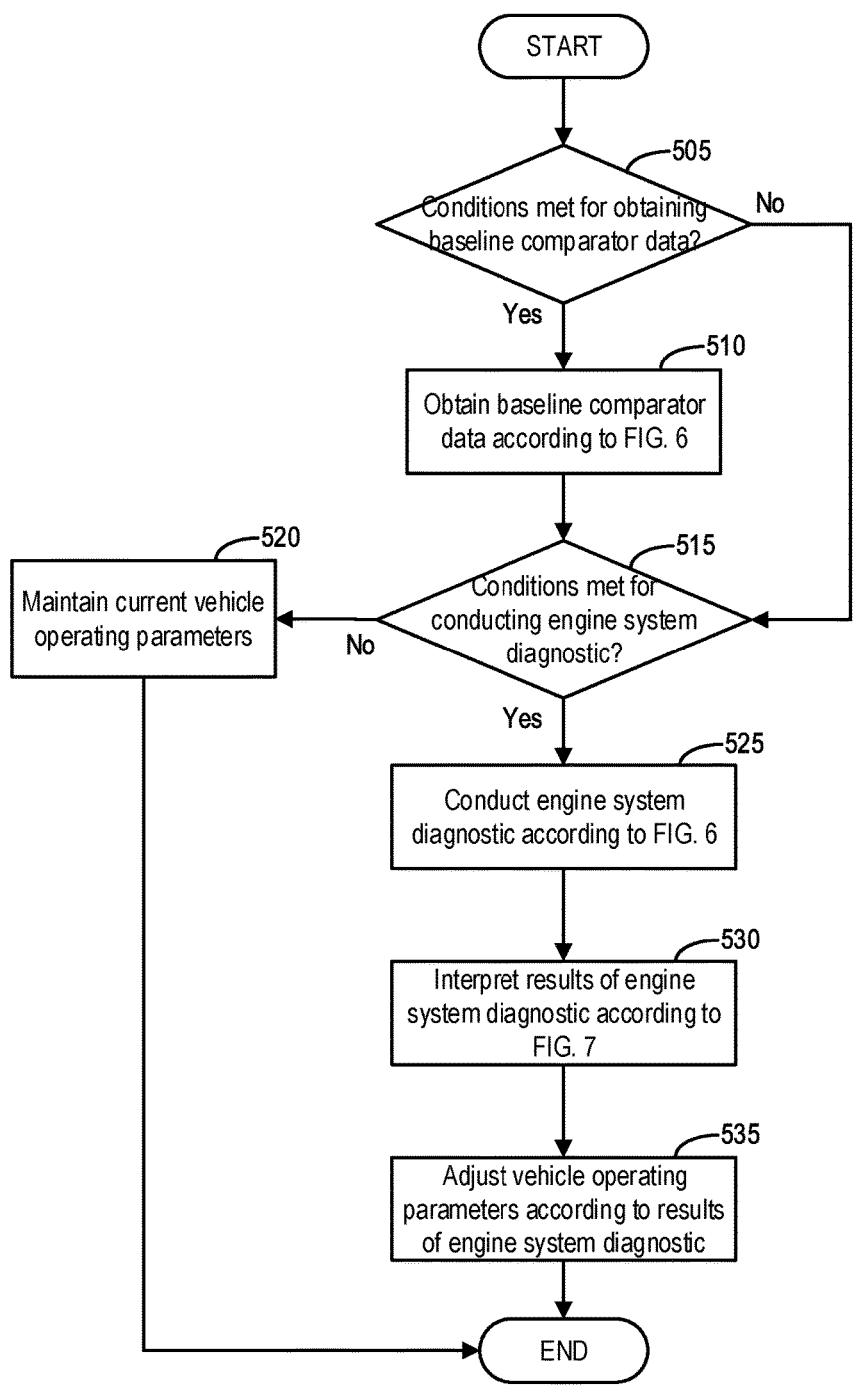
FIG. 5 shows a high level flowchart for indicating a presence or absence of degradation stemming from an intake manifold, exhaust system, or an engine.
Figure 6:
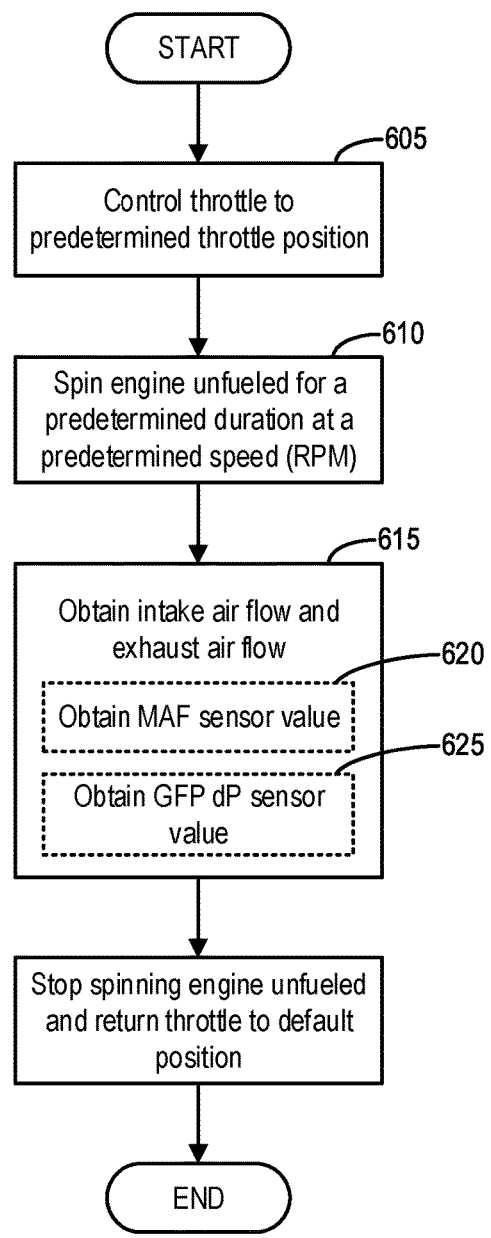
FIG. 6 shows a high level flowchart detailing steps for obtaining baseline comparator data and for conducting an engine system diagnostic, for use in the method of FIG. 5 above.

The following description relates to systems and methods for pinpointing sources of degradation stemming from either an intake manifold, exhaust system, or an engine of a vehicle. Such a method may include spinning or rotating an engine without fuel injection, where spinning the engine unfueled is conducted via an electric motor of a hybrid vehicle, such as the hybrid vehicle depicted at FIG. 1. To diagnose a source of degradation in an engine system (the engine system including the engine intake manifold, engine exhaust system, and engine), intake air flow and exhaust flow may be monitored under a set of predetermined conditions, and compared to a set of baseline intake air flow and exhaust flow measured under a substantially equivalent set of predetermined conditions. Measuring intake air flow may be conducted via a mass air flow (MAF) sensor positioned in the intake manifold, whereas measuring exhaust flow may be conducted via a gasoline particulate filter (GPF) differential pressure sensor, positioned in the exhaust system downstream of an exhaust manifold, as illustrated in FIG. 2. By comparing intake and exhaust flow measurements to baseline measurements conducted under conditions where degradation is not present in the engine system, sources of degradation may be pinpointed as to stemming from the intake manifold, exhaust system, or engine, as illustrated at FIGS. 3A-3C. In some examples, the set of predetermined conditions for conducting baseline intake and exhaust flow measurements and test intake and exhaust flow measurements may comprise an indication that the vehicle is not occupied. Thus, such measurements may in some examples be carried out in an autonomous vehicle that is not occupied, where FIG. 4 depicts an example autonomous vehicle control system. A method for pinpointing a source of degradation in an intake manifold, exhaust system, or engine is illustrated at FIG. 5. As discussed, such a method may include baseline measurements of intake air flow and exhaust flow, in addition to similar measurements during test conditions. Accordingly, a method for obtaining such measurements, for use in the method depicted at FIG. 5, is illustrated at FIG. 6. To interpret the results of such a diagnostic test, the results may be analyzed via a lookup table, such as the lookup table depicted above at FIG. 7. An example timeline for conducting such an engine system test diagnostic procedure is illustrated at FIG. 8.

Figure 1:
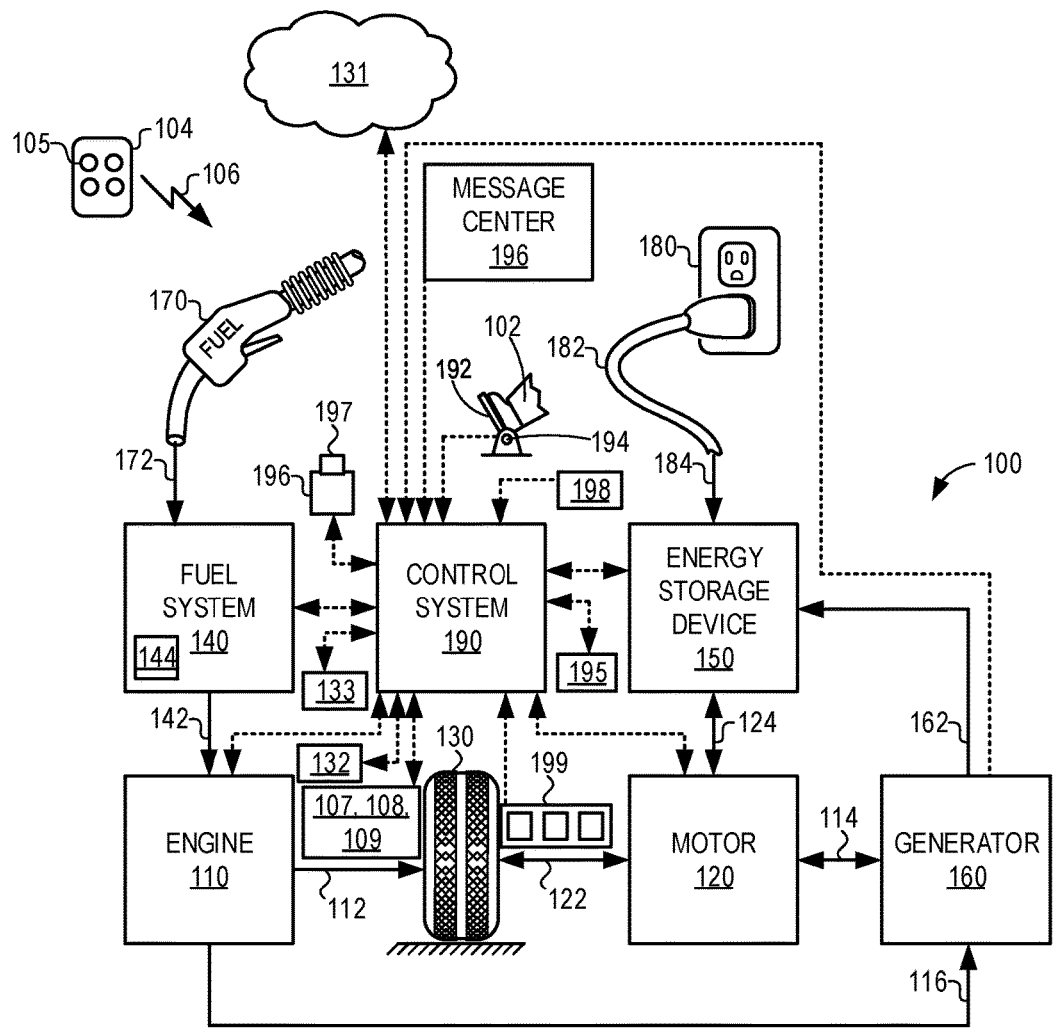
FIG. 1 schematically shows an example vehicle propulsion system.

FIG. 1 illustrates an example vehicle propulsion system 100. Vehicle propulsion system 100 includes a fuel burning engine 110 and a motor 120. As a non-limiting example, engine 110 comprises an internal combustion engine and motor 120 comprises an electric motor. Motor 120 may be configured to utilize or consume a different energy source than engine 110. For example, engine 110 may consume a liquid fuel (e.g., gasoline) to produce an engine output while motor 120 may consume electrical energy to produce a motor output. As such, a vehicle with propulsion system 100 may be referred to as a hybrid electric vehicle (HEV).

Vehicle propulsion system 100 may utilize a variety of different operational modes depending on operating conditions encountered by the vehicle propulsion system. Some of these modes may enable engine 110 to be maintained in an off state (i.e., set to a deactivated state) where combustion of fuel at the engine is discontinued. For example, under select operating conditions, motor 120 may propel the vehicle via drive wheel 130 as indicated by arrow 122 while engine 110 is deactivated.

During other operating conditions, engine 110 may be set to a deactivated state (as described above) while motor 120 may be operated to charge energy storage device 150. For example, motor 120 may receive wheel torque from drive wheel 130 as indicated by arrow 122 where the motor may convert the kinetic energy of the vehicle to electrical energy for storage at energy storage device 150 as indicated by arrow 124. This operation may be referred to as regenerative braking of the vehicle. Thus, motor 120 can provide a generator function in some examples. However, in other examples, generator 160 may instead receive wheel torque from drive wheel 130, where the generator may convert the kinetic energy of the vehicle to electrical energy for storage at energy storage device 150 as indicated by arrow 162.

During still other operating conditions, engine 110 may be operated by combusting fuel received from fuel system 140 as indicated by arrow 142. For example, engine 110 may be operated to propel the vehicle via drive wheel 130 as indicated by arrow 112 while motor 120 is deactivated. During other operating conditions, both engine 110 and motor 120 may each be operated to propel the vehicle via drive wheel 130 as indicated by arrows 112 and 122, respectively. A configuration where both the engine and the motor may selectively propel the vehicle may be referred to as a parallel type vehicle propulsion system. Note that in some examples, motor 120 may propel the vehicle via a first set of drive wheels and engine 110 may propel the vehicle via a second set of drive wheels.

In other examples, vehicle propulsion system 100 may be configured as a series type vehicle propulsion system, whereby the engine does not directly propel the drive wheels. Rather, engine 110 may be operated to power motor 120, which may in turn propel the vehicle via drive wheel 130 as indicated by arrow 122. For example, during select operating conditions, engine 110 may drive generator 160 as indicated by arrow 116, which may in turn supply electrical energy to one or more of motor 120 as indicated by arrow 114 or energy storage device 150 as indicated by arrow 162. As another example, engine 110 may be operated to drive motor 120 which may in turn provide a generator function to convert the engine output to electrical energy, where the electrical energy may be stored at energy storage device 150 for later use by the motor.

In still other examples, which will be discussed in detail below, motor 120 may in some examples be utilized to spin or rotate the motor in an unfueled configuration. More specifically, motor 120 may rotate the engine unfueled, using power from onboard energy storage device 150, which may include a battery, for example. In a case where motor 120 is used to rotate the engine unfueled, fuel injection to engine cylinders may be prevented, and spark may not be provided to each of the engine cylinders.

Fuel system 140 may include one or more fuel storage tanks 144 for storing fuel on-board the vehicle. For example, fuel tank 144 may store one or more liquid fuels, including but not limited to: gasoline, diesel, and alcohol fuels. In some examples, the fuel may be stored on-board the vehicle as a blend of two or more different fuels. For example, fuel tank 144 may be configured to store a blend of gasoline and ethanol (e.g., E10, E85, etc.) or a blend of gasoline and methanol (e.g., M10, M85, etc.), whereby these fuels or fuel blends may be delivered to engine 110 as indicated by arrow 142. Still other suitable fuels or fuel blends may be supplied to engine 110, where they may be combusted at the engine to produce an engine output. The engine output may be utilized to propel the vehicle as indicated by arrow 112 or to recharge energy storage device 150 via motor 120 or generator 160.

In some examples, energy storage device 150 may be configured to store electrical energy that may be supplied to other electrical loads residing on-board the vehicle (other than the motor), including cabin heating and air conditioning, engine starting, headlights, cabin audio and video systems, etc. As a non-limiting example, energy storage device 150 may include one or more batteries and/or capacitors.

Control system 190 may communicate with one or more of engine 110, motor 120, fuel system 140, energy storage device 150, and generator 160. Control system 190 may receive sensory feedback information from one or more of engine 110, motor 120, fuel system 140, energy storage device 150, and generator 160. Further, control system 190 may send control signals to one or more of engine 110, motor 120, fuel system 140, energy storage device 150, and generator 160 responsive to this sensory feedback. Control system 190 may receive an indication of an operator requested output of the vehicle propulsion system from a vehicle operator 102. For example, control system 190 may receive sensory feedback from pedal position sensor 194 which communicates with pedal 192. Pedal 192 may refer schematically to a brake pedal and/or an accelerator pedal. Furthermore, in some examples control system 190 may be in communication with a remote engine start receiver 195 (or transceiver) that receives wireless signals 106 from a key fob 104 having a remote start button 105. In other examples (not shown), a remote engine start may be initiated via a cellular telephone, or smartphone based system where a user's cellular telephone sends data to a server and the server communicates with the vehicle to start the engine. Energy storage device 150 may periodically receive electrical energy from a power source 180 residing external to the vehicle (e.g., not part of the vehicle) as indicated by arrow 184. As a non-limiting example, vehicle propulsion system 100 may be configured as a plug-in hybrid electric vehicle (HEV), whereby electrical energy may be supplied to energy storage device 150 from power source 180 via an electrical energy transmission cable 182. During a recharging operation of energy storage device 150 from power source 180, electrical transmission cable 182 may electrically couple energy storage device 150 and power source 180. While the vehicle propulsion system is operated to propel the vehicle, electrical transmission cable 182 may disconnected between power source 180 and energy storage device 150. Control system 190 may identify and/or control the amount of electrical energy stored at the energy storage device, which may be referred to as the state of charge (SOC).

In other examples, electrical transmission cable 182 may be omitted, where electrical energy may be received wirelessly at energy storage device 150 from power source 180. For example, energy storage device 150 may receive electrical energy from power source 180 via one or more of electromagnetic induction, radio waves, and electromagnetic resonance. As such, it should be appreciated that any suitable approach may be used for recharging energy storage device 150 from a power source that does not comprise part of the vehicle. In this way, motor 120 may propel the vehicle by utilizing an energy source other than the fuel utilized by engine 110.

Fuel system 140 may periodically receive fuel from a fuel source residing external to the vehicle. As a non-limiting example, vehicle propulsion system 100 may be refueled by receiving fuel via a fuel dispensing device 170 as indicated by arrow 172. In some examples, fuel tank 144 may be configured to store the fuel received from fuel dispensing device 170 until it is supplied to engine 110 for combustion. In some examples, control system 190 may receive an indication of the level of fuel stored at fuel tank 144 via a fuel level sensor. The level of fuel stored at fuel tank 144 (e.g., as identified by the fuel level sensor) may be communicated to the vehicle operator, for example, via a fuel gauge or indication in a vehicle instrument panel 196.

The vehicle propulsion system 100 may also include an ambient temperature/humidity sensor 198, and a roll stability control sensor, such as a lateral and/or longitudinal and/or yaw rate sensor(s) 199. The vehicle instrument panel 196 may include indicator light(s) and/or a text-based display in which messages are displayed to an operator. The vehicle instrument panel 196 may also include various input portions for receiving an operator input, such as buttons, touch screens, voice input/recognition, etc. For example, the vehicle instrument panel 196 may include a refueling button 197 which may be manually actuated or pressed by a vehicle operator to initiate refueling. For example, as described in more detail below, in response to the vehicle operator actuating refueling button 197, a fuel tank in the vehicle may be depressurized so that refueling may be performed.

Control system 190 may be communicatively coupled to other vehicles or infrastructures using appropriate communications technology, as is known in the art. For example, control system 190 may be coupled to other vehicles or infrastructures via a wireless network 131, which may comprise Wi-Fi, Bluetooth, a type of cellular service, a wireless data transfer protocol, and so on. Control system 190 may broadcast (and receive) information regarding vehicle data, vehicle diagnostics, traffic conditions, vehicle location information, vehicle operating procedures, etc., via vehicle-to-vehicle (V2V), vehicle-to-infrastructure-to-vehicle (V2I2V), and/or vehicle-to-infrastructure (V2I) technology. The communication and the information exchanged between vehicles can be either direct between vehicles, or can be multi-hop. In some examples, longer range communications (e.g. WiMax) may be used in place of, or in conjunction with, V2V or V2I2V, to extend the coverage area by a few miles. In still other examples, vehicle control system 190 may be communicatively coupled to other vehicles or infrastructures via a wireless network 131 and the internet (e.g. cloud), as is commonly known in the art.

Vehicle system 100 may also include an on-board navigation system 132 (for example, a Global Positioning System) that an operator of the vehicle may interact with. The navigation system 132 may include one or more location sensors for assisting in estimating vehicle speed, vehicle altitude, vehicle position/location, etc. This information may be used to infer engine operating parameters, such as local barometric pressure. As discussed above, control system 190 may further be configured to receive information via the internet or other communication networks. Information received from the GPS may be cross-referenced to information available via the internet to determine local weather conditions, local vehicle regulations, etc. In one example, information received from the GPS may be utilized in conjunction with route learning methodology, such that routes commonly traveled by a vehicle may be learned by the vehicle control system 190. In some examples, other sensors, such as lasers, radar, sonar, acoustic sensors, etc, (e.g. 133) may be additionally or alternatively utilized in conjunction with the onboard navigation system to conduct route learning of commonly traveled routes by the vehicle.

Vehicle system 100 may also include sensors dedicated to indicating the occupancy-state of the vehicle, for example seat load cells 107, door sensing technology 108, and onboard cameras 109.

FIG. 2 shows a schematic depiction of a vehicle system 206. It may be understood that vehicle system 206 may comprise the same vehicle system as vehicle system 100 depicted at FIG. 1. The vehicle system 206 includes an engine system 208 coupled to an emissions control system 251 and a fuel system 218. It may be understood that fuel system 218 may comprise the same fuel system as fuel system 140 depicted at FIG. 1. Emission control system 251 includes a fuel vapor container or canister 222 which may be used to capture and store fuel vapors. In some examples, vehicle system 206 may be a hybrid electric vehicle system.

The engine system 208 may include an engine 110 having a plurality of cylinders 230. While not explicitly shown, it may be understood that each cylinder may include one or more intake valve(s) and one or more exhaust valve(s). The engine 110 includes an engine air intake 223 and an engine exhaust 225. The engine air intake 223 includes a throttle 262 in fluidic communication with engine intake manifold 244 via an intake passage 242. The throttle 262 may comprise an electronic throttle, which may be controlled via the vehicle controller sending a signal to actuate the throttle to a desired position. In such an example where the throttle is electronic, power to control the throttle to the desired position may be from an onboard energy storage device (e.g. 150), such as a battery. Further, engine air intake 223 may include an air box and filter 215 positioned upstream of throttle 262. The engine exhaust system 225 includes an exhaust manifold 248 leading to an exhaust passage 235 that routes exhaust gas to the atmosphere. The engine exhaust system 225 may include one or more exhaust catalyst 270, which may be mounted in a close-coupled position in the exhaust. One or more emission control devices may include a three-way catalyst, lean NOx trap, diesel particulate filter, oxidation catalyst, etc. It will be appreciated that other components may be included in the engine such as a variety of valves and sensors. For example, a barometric pressure sensor 213 may be included in the engine intake. In one example, barometric pressure sensor 213 may be a manifold air pressure (MAP) sensor and may be coupled to the engine intake downstream of throttle 262. Barometric pressure sensor 213 may rely on part throttle or full or wide open throttle conditions, e.g., when an opening amount of throttle 262 is greater than a threshold, in order accurately determine BP. Alternatively, MAP may be inferred from alternate engine operating conditions, such as mass air flow (MAF), as measured by MAF sensor 210 coupled to the intake manifold.

Engine exhaust system 225 may further include a gasoline particulate filter (GPF) 217. GPF 217 may comprise a particulate filter, hydrocarbon trap, a catalyzed wash coat, or combination thereof. In some examples, during operation of engine 110, GPF 217 may be periodically regenerated by operating at least one cylinder of the engine within a particular air-fuel ratio to increase a temperature of GPF 217, such that retained hydrocarbons and soot particles may be oxidized.

In some examples, temperature sensor 226 may be positioned upstream from the inlet of GPF 217 and temperature sensor 229 may be positioned downstream of GPF 217. Temperature sensors 226 and 229 may be used to assess the temperature of GPF 217 for regeneration purposes, for example. Furthermore, pressure in the exhaust system may be assessed by pressure sensor 263. Pressure sensor 263 may be a differential pressure sensor positioned upstream and downstream of GPF 217, for example. Pressure sensor 263 may be used to determine pressure at the inlet of GPF 217 in order to assess operating conditions for air to be introduced to the inlet of GPF 217 for regeneration. Furthermore, in some examples, soot sensor 268 may be positioned downstream of GPF 217, to assess the level of soot that is released from GPF 217. Soot sensor 268 may be used to diagnose operation of GPF 217, among other functions.

Fuel system 218 may include a fuel tank 220 coupled to a fuel pump system 221. It may be understood that fuel tank 220 may comprise the same fuel tank as fuel tank 144 depicted above at FIG. 1. The fuel pump system 221 may include one or more pumps for pressurizing fuel delivered to the injectors of engine 110, such as the example injector 266 shown. While only a single injector 266 is shown, additional injectors are provided for each cylinder. It will be appreciated that fuel system 218 may be a return-less fuel system, a return fuel system, or various other types of fuel system. Fuel tank 220 may hold a plurality of fuel blends, including fuel with a range of alcohol concentrations, such as various gasoline-ethanol blends, including E10, E85, gasoline, etc., and combinations thereof. A fuel level sensor 234 located in fuel tank 220 may provide an indication of the fuel level ("Fuel Level Input") to controller 212. As depicted, fuel level sensor 234 may comprise a float connected to a variable resistor. Alternatively, other types of fuel level sensors may be used.

Vapors generated in fuel system 218 may be routed to an evaporative emissions control system 251 which includes a fuel vapor canister 222 via vapor recovery line 231, before being purged to the engine air intake 223. Vapor recovery line 231 may be coupled to fuel tank 220 via one or more conduits and may include one or more valves for isolating the fuel tank during certain conditions. For example, vapor recovery line 231 may be coupled to fuel tank 220 via one or more or a combination of conduits 271, 273, and 275.

Further, in some examples, one or more fuel tank vent valves may be positioned in conduits 271, 273, or 275. Among other functions, fuel tank vent valves may allow a fuel vapor canister of the emissions control system to be maintained at a low pressure or vacuum without increasing the fuel evaporation rate from the tank (which would otherwise occur if the fuel tank pressure were lowered). For example, conduit 271 may include a grade vent valve (GVV) 287, conduit 273 may include a fill limit venting valve (FLVV) 285, and conduit 275 may include a grade vent valve (GVV) 283. Further, in some examples, recovery line 231 may be coupled to a fuel filler system 219. In some examples, fuel filler system may include a fuel cap 205 for sealing off the fuel filler system from the atmosphere. Refueling system 219 is coupled to fuel tank 220 via a fuel filler pipe or neck 211.

Further, refueling system 219 may include refueling lock 245. In some examples, refueling lock 245 may be a fuel cap locking mechanism. The fuel cap locking mechanism may be configured to automatically lock the fuel cap in a closed position so that the fuel cap cannot be opened. For example, the fuel cap 205 may remain locked via refueling lock 245 while pressure or vacuum in the fuel tank is greater than a threshold. In response to a refuel request, e.g., a vehicle operator initiated request, the fuel tank may be depressurized and the fuel cap unlocked after the pressure or vacuum in the fuel tank falls below a threshold. A fuel cap locking mechanism may be a latch or clutch, which, when engaged, prevents the removal of the fuel cap. The latch or clutch may be electrically locked, for example, by a solenoid, or may be mechanically locked, for example, by a pressure diaphragm.

In some examples, refueling lock 245 may be a filler pipe valve located at a mouth of fuel filler pipe 211. In such examples, refueling lock 245 may not prevent the removal of fuel cap 205. Rather, refueling lock 245 may prevent the insertion of a refueling pump into fuel filler pipe 211. The filler pipe valve may be electrically locked, for example by a solenoid, or mechanically locked, for example by a pressure diaphragm.

In some examples, refueling lock 245 may be a refueling door lock, such as a latch or a clutch which locks a refueling door located in a body panel of the vehicle. The refueling door lock may be electrically locked, for example by a solenoid, or mechanically locked, for example by a pressure diaphragm.

In examples where refueling lock 245 is locked using an electrical mechanism, refueling lock 245 may be unlocked by commands from controller 212, for example, when a fuel tank pressure decreases below a pressure threshold. In examples where refueling lock 245 is locked using a mechanical mechanism, refueling lock 245 may be unlocked via a pressure gradient, for example, when a fuel tank pressure decreases to atmospheric pressure.

Emissions control system 251 may include one or more emissions control devices, such as one or more fuel vapor canisters 222 filled with an appropriate adsorbent 286b, the canisters are configured to temporarily trap fuel vapors (including vaporized hydrocarbons) during fuel tank refilling operations and "running loss" (that is, fuel vaporized during vehicle operation). In one example, the adsorbent 286b used is activated charcoal. Emissions control system 251 may further include a canister ventilation path or vent line 227 which may route gases out of the canister 222 to the atmosphere when storing, or trapping, fuel vapors from fuel system 218.

Canister 222 may include a buffer 222a (or buffer region), each of the canister and the buffer comprising the adsorbent. As shown, the volume of buffer 222a may be smaller than (e.g., a fraction of) the volume of canister 222. The adsorbent 286a in the buffer 222a may be same as, or different from, the adsorbent in the canister (e.g., both may include charcoal). Buffer 222a may be positioned within canister 222 such that during canister loading, fuel tank vapors are first adsorbed within the buffer, and then when the buffer is saturated, further fuel tank vapors are adsorbed in the canister. In comparison, during canister purging, fuel vapors are first desorbed from the canister (e.g., to a threshold amount) before being desorbed from the buffer. In other words, loading and unloading of the buffer is not linear with the loading and unloading of the canister. As such, the effect of the canister buffer is to dampen any fuel vapor spikes flowing from the fuel tank to the canister, thereby reducing the possibility of any fuel vapor spikes going to the engine. One or more temperature sensors 232 may be coupled to and/or within canister 222. As fuel vapor is adsorbed by the adsorbent in the canister, heat is generated (heat of adsorption). Likewise, as fuel vapor is desorbed by the adsorbent in the canister, heat is consumed. In this way, the adsorption and desorption of fuel vapor by the canister may be monitored and estimated based on temperature changes within the canister.

Vent line 227 may also allow fresh air to be drawn into canister 222 when purging stored fuel vapors from fuel system 218 to engine intake 223 via purge line 228 and purge valve 261. For example, purge valve 261 may be normally closed but may be opened during certain conditions so that vacuum from engine intake manifold 244 is provided to the fuel vapor canister for purging. In some examples, vent line 227 may include an air filter 259 disposed therein upstream of a canister 222.

In some examples, the flow of air and vapors between canister 222 and the atmosphere may be regulated by a canister vent valve 297 coupled within vent line 227. When included, the canister vent valve 297 may be a normally open valve, so that fuel tank isolation valve 252 (FTIV) may control venting of fuel tank 220 with the atmosphere. FTIV 252 may be positioned between the fuel tank and the fuel vapor canister 222 within conduit 278. FTIV 252 may be a normally closed valve, that when opened, allows for the venting of fuel vapors from fuel tank 220 to fuel vapor canister 222. Fuel vapors may then be vented to atmosphere, or purged to engine intake system 223 via canister purge valve 261. As will be discussed in detail below, in some example the FTIV may not be included, whereas in other examples, an FTIV may be included.

Fuel system 218 may be operated by controller 212 in a plurality of modes by selective adjustment of the various valves and solenoids. It may be understood that control system 214 may comprise the same control system as control system 190 depicted above at FIG. 1. For example, the fuel system may be operated in a fuel vapor storage mode (e.g., during a fuel tank refueling operation and with the engine not combusting air and fuel), wherein the controller 212 may open isolation valve 252 (when included) while closing canister purge valve (CPV) 261 to direct refueling vapors into canister 222 while preventing fuel vapors from being directed into the intake manifold.

As another example, the fuel system may be operated in a refueling mode (e.g., when fuel tank refueling is requested by a vehicle operator), wherein the controller 212 may open isolation valve 252 (when included), while maintaining canister purge valve 261 closed, to depressurize the fuel tank before allowing enabling fuel to be added therein. As such, isolation valve 252 (when included) may be kept open during the refueling operation to allow refueling vapors to be stored in the canister. After refueling is completed, the isolation valve may be closed.

As yet another example, the fuel system may be operated in a canister purging mode (e.g., after an emission control device light-off temperature has been attained and with the engine combusting air and fuel), wherein the controller 212 may open canister purge valve 261 while closing isolation valve 252 (when included). Herein, the vacuum generated by the intake manifold of the operating engine may be used to draw fresh air through vent 227 and through fuel vapor canister 222 to purge the stored fuel vapors into intake manifold 244. In this mode, the purged fuel vapors from the canister are combusted in the engine. The purging may be continued until the stored fuel vapor amount in the canister is below a threshold.

Controller 212 may comprise a portion of a control system 214. In some examples, control system 214 may be the same as control system 190, illustrated in FIG. 1. Control system 214 is shown receiving information from a plurality of sensors 216 (various examples of which are described herein) and sending control signals to a plurality of actuators 281 (various examples of which are described herein). As one example, sensors 216 may include exhaust gas sensor 237 located upstream of the emission control device 270, temperature sensor 233, pressure sensor 291, pressure sensor 282, and canister temperature sensor 232. Other sensors such as pressure, temperature, air/fuel ratio, and composition sensors may be coupled to various locations in the vehicle system 206. As another example, the actuators may include throttle 262, fuel tank isolation valve 252, canister purge valve 261, and canister vent valve 297. The control system 214 may include a controller 212. The controller may receive input data from the various sensors, process the input data, and trigger the actuators in response to the processed input data based on instruction or code programmed therein corresponding to one or more routines. Example control routines are described herein with regard to FIGS. 5-6.

In some examples, the controller may be placed in a reduced power mode or sleep mode, wherein the controller maintains essential functions only, and operates with a lower battery consumption than in a corresponding awake mode. For example, the controller may be placed in a sleep mode following a vehicle-off event in order to perform a diagnostic routine at a duration after the vehicle-off event. The controller may have a wake input that allows the controller to be returned to an awake mode based on an input received from one or more sensors. For example, the opening of a vehicle door may trigger a return to an awake mode. In other examples, particularly with regard to the methods depicted in FIGS. 5-6, the controller may be required to be awake in order to conduct such methods. For example, a wakeup capability may enable a circuit to wake the controller in order to obtain baseline comparator data, or to conduct an engine system diagnostic, as will be discussed in further detail below.

Undesired evaporative emissions detection routines may be intermittently performed by controller 212 on fuel system 218 and/or evaporative emissions system 251 to confirm that undesired evaporative emissions are not present in the fuel system and/or evaporative emissions system. As such, evaporative emissions detection routines may be performed while the engine is off (engine-off test) using engine-off natural vacuum (EONV) generated due to a change in temperature and pressure at the fuel tank following engine shutdown and/or with vacuum supplemented from a vacuum pump. Alternatively, evaporative emissions detection routines may be performed while the engine is running by operating a vacuum pump and/or using engine intake manifold vacuum. In some configurations, a canister vent valve (CVV) 297 may be coupled within vent line 227. CVV 297 may function to adjust a flow of air and vapors between canister 222 and the atmosphere. The CVV may also be used for diagnostic routines. When included, the CVV may be opened during fuel vapor storing operations (for example, during fuel tank refueling and while the engine is not running) so that air, stripped of fuel vapor after having passed through the canister, can be pushed out to the atmosphere. Likewise, during purging operations (for example, during canister regeneration and while the engine is running), the CVV may be opened to allow a flow of fresh air to strip the fuel vapors stored in the canister. In some examples, CVV 297 may be a solenoid valve wherein opening or closing of the valve is performed via actuation of a canister vent solenoid. In particular, the canister vent valve may be an open that is closed upon actuation of the canister vent solenoid. In some examples, CVV 297 may be configured as a latchable solenoid valve. In other words, when the valve is placed in a closed configuration, it latches closed without requiring additional current or voltage. For example, the valve may be closed with a 100 ms pulse, and then opened at a later time point with another 100 ms pulse. In this way, the amount of battery power required to maintain the CVV closed is reduced. In particular, the CVV may be closed while the vehicle is off, thus maintaining battery power while maintaining the fuel emissions control system sealed from atmosphere.

In another example, an engine system diagnostic may be conducted in order to determine whether a source of degradation stems from an intake manifold of the engine, an exhaust system of the engine, or the engine itself. Such an example will be discussed in detail below with regard to the methods depicted at FIGS. 5-6. Discussed herein, degradation of the intake manifold may refer to a puncture, crack, degraded gasket, loose coupling, or air leak in the intake manifold. Degradation of the exhaust system may similarly refer to a puncture, crack, degraded gasket, loose coupling, or exhaust leak in the exhaust system. It may be understood that degradation of the exhaust system may refer to the engine system upstream of the GPF (e.g. 217), and downstream of the engine (e.g. 110). Finally, degradation of the engine may refer to intake/exhaust valves that are not sealing properly, undesired camshaft timing, compression issues, or any other engine-specific issues which may result in the engine not pumping as effectively as expected or demanded.

Turning now to FIGS. 3A-3C, they illustrate examples of sources of degradation stemming from an intake manifold, exhaust system, or engine, respectively. Accordingly, FIGS. 3A-3C illustrate simplified block diagrams of an engine system comprising a MAF sensor 210, intake manifold 244, engine 110, exhaust system 225, GPF 217, and differential pressure sensor 263. As such, FIGS. 3A-3C represent simplified block diagrams of the engine system depicted above at FIG. 2. In each of FIGS. 3A-3C, as will be elaborated below, a source of degradation is illustrated, denoted as 310a, 310b, and 310c.

Turning now to FIG. 3A, it shows an example where a source of degradation 310a is stemming from intake manifold 244. In such an example, the source of degradation 310a is not directly observable via MAF sensor 210, as the source of degradation is downstream of MAF sensor 210. However, while the engine is in operation, unmetered air may be drawn into the engine via the source of degradation. Thus, it may be understood that additional air (in addition to that drawn through the intake passage (e.g. 242) may be drawn into the engine, and accordingly pressure in the exhaust system may be greater than expected, as monitored by the differential pressure sensor 263. Accordingly, as will be discussed in further detail below with regard to FIGS. 5-8, it may be possible to diagnose a source of degradation in the intake manifold 244 if a mass air flow as indicated via MAF sensor 210 is substantially equivalent to an expected mass air flow under a set of predetermined conditions, but where exhaust flow (e.g. pressure in the exhaust system) as indicated by differential pressure sensor 263, is greater than an expected exhaust flow under the same (or substantially equivalent) set of predetermined conditions.

Turning now to FIG. 3B, it shows an example where a source of degradation 310b is stemming from the exhaust system 225. In such an example, the source of degradation is not directly observable via MAF sensor 210, or differential pressure sensor 263. However, while the engine is in operation, exhaust flow may be pushed or forced to atmosphere via the source of degradation 310b, resulting in an overall less exhaust flow as monitored via the differential pressure sensor 263. Accordingly, as will be discussed in further detail below with regard to FIGS. 5-8, it may be possible to diagnose a source of degradation in the exhaust system 225 if a mass air flow as indicated via MAF sensor 210 is substantially equivalent to an expected mass air flow under a set of predetermined conditions, but where exhaust flow (e.g. pressure in the exhaust system) as indicated by differential pressure sensor 263, is less than an expected exhaust flow under the same (or substantially equivalent) set of predetermined conditions.

Turning now to FIG. 3C, it shows an example where a source of degradation 310c is stemming from engine 110. As mentioned above, a source of degradation 310c stemming from the engine 110 may comprise intake/exhaust valves that are not sealing properly, undesired camshaft timing, compression issues, or any other engine-specific issues which may result in the engine not pumping as effectively as expected or demanded. In such an example, MAF sensor 210 may not directly be used to infer a source of degradation stemming from the engine, and similarly differential pressure sensor 263 may not directly be used to infer such a source of degradation. However, an engine with a source of degradation may not pump as efficiently as expected, and as such, an amount of air drawn into the intake passage (e.g. 242) may be lower than expected under a set of predetermined conditions. Similarly, because less air overall was drawn into the engine via the intake passage, then less exhaust flow may occur as a result. Accordingly, as will be discussed in further detail below with regard to FIGS. 5-8, it may be possible to diagnose a source of degradation stemming from engine 110 if intake mass air flow as indicated by MAF sensor 210 is substantially equivalent to exhaust flow as indicated by differential pressure sensor 263, but where both intake mass air flow and exhaust flow are lower than expected under a set of predetermined conditions.

The set of predetermined conditions, as discussed above with regard to FIGS. 3A-3C may include engine speed at a predetermined speed (e.g. predetermined RPM), a position of a throttle (e.g. 262) at a predetermined angle or level of opening, the engine being rotated or spun unfueled via power from an onboard energy storage device (e.g. 150), etc. Furthermore, as discussed above, "expected" amounts of air flow in the intake manifold and exhaust system may comprise air flow amounts that have been previously established during conditions where no source of degradation is indicated. In other words, as will be discussed in further detail below, expected amounts of air flow in the intake manifold and exhaust system may comprise a baseline air flow in the intake manifold and exhaust flow in the exhaust system, under a substantially equivalent set of predetermined conditions as that discussed above with regard to FIGS. 3A-3C.

As discussed, one of the set of predetermined conditions may include rotating or spinning the engine unfueled to establish baseline, or expected, air flow in the intake manifold and exhaust system under conditions where degradation is not indicated. Furthermore, when conducting the engine system diagnostic comprising comparing values obtained via the MAF sensor 210 and differential pressure sensor 263, the predetermined conditions may similarly include rotating or spinning the engine unfueled. Accordingly, to avoid customer dissatisfaction due to the engine spinning without being fueled, such an engine system diagnostic may execute under conditions where a vehicle operator and passengers are not indicated to be in the vehicle. Examples may include a remote start event when the vehicle is not occupied, a "wake-up" of the vehicle controller some predetermined duration after a key off event where the vehicle is not occupied, etc. In still another example, the engine system diagnostic may be conducted in an autonomous vehicle in which the vehicle is indicated to be unoccupied. In each of the above-mentioned examples, vehicle occupancy may be indicated by one or more of seat load cells (e.g. 107, door sensing technology (e.g. 108), and/or onboard camera(s) (e.g. 109).

As the engine system diagnostic discussed above may be conducted in a vehicle configured as an autonomous vehicle, an example autonomous driving system is discussed below with regard to FIG. 4. FIG. 4 is a block diagram of an example autonomous driving system 400 that may operate the vehicle system 100, described above at FIG. 1. Herein, the vehicle system 100 will be referred to simply as a "vehicle". The autonomous driving system 400, as shown, includes a user interface device 410, a navigation system 415, at least one autonomous driving sensor 420, and an autonomous mode controller 425. It may be understood that the onboard navigation system 415 may be the same as the onboard navigation system 132 depicted above at FIG. 1.

The user interface device 410 may be configured to present information to vehicle occupants, under conditions wherein a vehicle occupant may be present. However, it may be understood that the vehicle may be operated autonomously in the absence of vehicle occupants, under certain conditions. The presented information may include audible information or visual information. Moreover, the user interface device 410 may be configured to receive user inputs. Thus, the user interface device 410 may be located in the passenger compartment (not shown) of the vehicle. In some possible approaches, the user interface device 410 may include a touch-sensitive display screen.

The navigation system 415 may be configured to determine a current location of the vehicle using, for example, a Global Positioning System (GPS) receiver configured to triangulate the position of the vehicle relative to satellites or terrestrial based transmitter towers. The navigation system 415 may be further configured to develop routes from the current location to a selected destination, as well as display a map and present driving directions to the selected destination via, for example, the user interface device 410.

The autonomous driving sensors 420 may include any number of devices configured to generate signals that help navigate the vehicle. Examples of autonomous driving sensors 420 may include a radar sensor, a lidar sensor, a vision sensor (e.g. a camera), vehicle to vehicle infrastructure networks, or the like. The autonomous driving sensors 420 may enable the vehicle to "see" the roadway and vehicle surroundings, and/or negotiate various obstacles while the vehicle 100 is operating in autonomous mode. The autonomous driving sensors 420 may be configured to output sensor signals to, for example, the autonomous mode controller 425.

The autonomous mode controller 425 may be configured to control one or more subsystems 430 while the vehicle is operating in the autonomous mode. Examples of subsystems 430 that may be controlled by the autonomous mode controller 425 may include a brake subsystem, a suspension subsystem, a steering subsystem, and a powertrain subsystem. The autonomous mode controller 425 may control any one or more of these subsystems 430 by outputting signals to control units associated with subsystems 430. In one example, the brake subsystem may comprise an anti-lock braking subsystem, configured to apply a braking force to one or more of wheels (e.g. 135). Discussed herein, applying the braking force to one or more of the vehicle wheels may be referred to as activating the brakes. To autonomously control the vehicle, the autonomous mode controller 425 may output appropriate commands to the subsystems 430. The commands may cause the subsystems to operate in accordance with the driving characteristics associated with the selected driving mode. For example, driving characteristics may include how aggressively the vehicle accelerates and decelerates, how much space the vehicle leaves behind a front vehicle, how frequently the autonomous vehicle changes lanes, etc.

Thus, a system for a vehicle may comprise an engine system including an intake manifold, an exhaust system, and an engine. A mass air flow sensor may be positioned in the intake manifold, and a differential pressure sensor may be positioned in the exhaust system, the differential pressure sensor configured to measure a pressure difference across a gasoline particulate filter positioned in the exhaust system. The system may include a motor, capable of rotating the engine unfueled. The system may further include a controller, storing instructions in non-transitory memory that, when executed, cause the controller to, in a first condition, obtain a set of baseline measurements of intake air flow and exhaust flow via the mass air flow sensor and the differential pressure sensor, respectively. In a second condition, the system may obtain a set of test measurements of intake air flow and exhaust flow during conducting an engine system diagnostic, which includes indicating a presence or absence of a degradation source stemming from one of the intake manifold, the exhaust system, or the engine. In such an example, the presence or absence of the degradation source may be based on comparing both 1) the baseline measurements of intake air flow and the test measurements of intake air flow obtained during both the first and second conditions, respectively, to one another, and 2) the baseline measurements of exhaust flow and the test measurements of exhaust flow obtained during both the first and second conditions, respectively, to one another.

In such a system, the controller may include additional instructions to 1) indicate the presence of the degradation source in the intake manifold responsive to the test measurements of intake air flow being substantially equivalent to the baseline measurements of intake flow, but where the test measurements of exhaust flow are greater than the baseline measurements of exhaust flow, 2) indicate the presence of the degradation source in the exhaust system responsive to the test measurements of intake air flow being substantially equivalent to the baseline measurements of intake air flow, but where the test measurements of exhaust flow is lower than the baseline measurements of exhaust flow, and 3) indicate the presence of the degradation source in the engine responsive to both the test measurements of intake air flow being lower than the baseline measurements of intake air flow, and the test measurements of exhaust flow being lower than the baseline measurements of exhaust flow.

Such a system may further comprise a throttle positioned in the intake manifold, where the controller may store further instructions to, in both the first and second conditions, rotate the engine unfueled via the motor, for a predetermined duration, with the throttle controlled to a predetermined position to allow air to be drawn into the engine while the engine is being rotated unfueled.

Such a system may further comprise an intake air filter positioned upstream of the throttle, and wherein the controller stores additional instructions to obtain the set of test measurements of intake air flow and exhaust flow in the second condition responsive to an indication that the set of baseline measurements of intake air flow and exhaust flow have been obtained in the first condition, and further responsive to an indication that the gasoline particulate filter has not been regenerated and that the intake air filter has not been replaced since obtaining the set of baseline measurements of intake air flow and exhaust flow in the first condition.

Such a system may further comprise additional instructions to obtain the set of test measurements of intake air flow and exhaust flow and obtain the set of baseline measurements of intake air flow and exhaust flow responsive to an indication that the vehicle is not occupied in both the first and second conditions.

Such a system may further comprise additional instructions to prevent regeneration of the gasoline particulate filter responsive to obtaining the set of baseline measurements of intake air flow and exhaust flow in the first condition, provided that a pressure difference across the gasoline particulate filter is not above a threshold pressure difference.

Such a system may further comprise additional instructions to again obtain the set of baseline measurements of intake air flow and exhaust flow prior to the second condition, responsive to the gasoline particulate filter being regenerated subsequent to the first condition and prior to the second condition.

It may be understood that in the above example of a system, the two conditions are not mutually exclusive. In other words, there would be no motivation to execute the first condition, without a goal of executing the second condition. More specifically, there would be no reason for obtaining the set of baseline measurements of intake air flow and exhaust flow under the conditions set out herein for the first condition, if the second condition were not subsequently executed.

Turning now to FIG. 5, a high level example method 500 for conducting an engine system diagnostic, is shown. More specifically, method 500 may be used to diagnose the presence or absence of degradation stemming from an intake manifold, exhaust system, or engine of a vehicle, by comparing intake air flow and exhaust flow under a set of predetermined conditions to a baseline intake air flow and exhaust flow (the baseline intake air flow and exhaust flow obtained under a substantially equivalent set of predetermined conditions). In this way, sources of degradation may be pinpointed as to being either in the intake manifold, exhaust system, or engine compartment. By pinpointing a source of degradation, repair procedures may be streamlined, and issues related to the engine system may be diagnosed rapidly and precisely, which may result in an increased lifespan of engine system componentry.

Method 500 will be described with reference to the systems described herein and shown in FIGS. 1-4, though it should be understood that similar methods may be applied to other systems without departing from the scope of this disclosure. Method 500 may be carried out by a controller, such as controller 212 in FIG. 2, and may be stored at the controller as executable instructions in non-transitory memory. Instructions for carrying out method 500 and the rest of the methods included herein may be executed by the controller based on instructions stored on a memory of the controller and in conjunction with signals received from sensors of the engine system, such as the sensors described above with reference to FIGS. 1-4. The controller may employ engine system actuators, such as motor (e.g. 120), throttle (e.g. 262), canister purge valve (e.g. 261), etc., according to the method below.

Method 500 begins at 505 and may include indicating whether conditions are met for obtaining baseline comparator data for the engine system diagnostic. Conditions being met for obtaining baseline comparator data may include an indication that the vehicle is not occupied. As discussed above, seat load cells, onboard camera(s), and/or door sensing technology may be utilized to ensure that the vehicle is not occupied. Baseline comparator data may be thus obtained responsive to a remote start event, or a wakeup of the controller a predetermined duration after a key-off event, or in a case where the vehicle comprises an autonomous vehicle that is unoccupied. More specifically, if the vehicle is in operation, for example if the vehicle is being propelled via either a motor (e.g. 120), engine (e.g. 110), or some combination thereof, conditions may not be indicated to be met for obtaining baseline comparator data for the engine system diagnostic. Still further, conditions being indicated to be met at 505 may include an indication that a source of degradation is not already indicated to be present in the intake manifold, exhaust system, or engine of the vehicle.

Furthermore, conditions being met at 505 for obtaining baseline comparator data may include an indication that baseline comparator data has not been obtained for a predetermined duration of time since a prior baseline comparator data measurement. In some examples, such a predetermined duration of time may comprise 1 day, greater than 1 day but less than 2 days, greater than 2 days, etc. If, at 505, it is indicated that conditions are indicated to be met for obtaining baseline comparator data, method 500 may proceed to 510, where baseline comparator data may be obtained according to the method 600 depicted at FIG. 6.

Alternatively, if conditions are not indicated to be met at 505 for obtaining baseline comparator data, method 500 may proceed to 515, and may include indicating whether conditions are met for conducting the engine system diagnostic. Conditions being met for conducting the engine system diagnostic may similarly include an indication that the vehicle is not occupied, which may include a remote start event, a controller wake-up a predetermined duration after a key-off event, or an unoccupied autonomous vehicle. Furthermore, conditions being met for conducting the engine system diagnostic at 515 may include an indication that baseline comparator data has been obtained within a threshold duration of the engine system diagnostic that is desired to be conducted at 515. In some examples, the threshold duration since baseline comparator data has been obtained may comprise 1 day or less, greater than 1 day but less than 2 days, greater than 2 days but less than three days, etc. Still further, conditions being met for conducting the engine system diagnostic at 515 may include an indication that an air intake system filter (e.g. 215) has not been replaced since baseline comparator data has been obtained, and may further include an indication that a GPF (e.g. 217) has not been regenerated since the baseline comparator data was obtained. Another example includes an indication that a source of degradation is not already indicated to be present in the intake manifold, exhaust system, or engine of the vehicle.

In still further examples, conditions being met for conducting the engine system diagnostic may include an indication of a disturbance to an air-fuel ratio, as monitored via an exhaust gas sensor (e.g. 237). For example, if during a drive cycle where the engine is operating (e.g. combusting air and fuel), it is indicated that the engine system is suddenly running lean (or rich), one possibility may be that there is a source of degradation stemming from either the intake manifold, exhaust system, or engine. Accordingly, if the engine system suddenly indicates an unexpected air-fuel ratio, then such an indication may be stored at the controller. Such an indication being stored at the controller may trigger the engine system diagnostic to be conducted, provided that all conditions are met for conducting the engine system diagnostic at step 515 of method 500.

If, at step 515, it is indicated that conditions are not met for conducting the engine system diagnostic, method 500 may proceed to 520, and may include maintaining current vehicle operating parameters. For example, if the vehicle is not in operation, with the engine off (not combusting air and fuel), and where the motor is not being utilized to propel the vehicle, then such conditions may be maintained. Alternatively, if the vehicle is in operation, then current vehicle operating parameters may be maintained. In an example case where an air-fuel ratio disturbance was indicated, and thus an engine system diagnostic is desired, but where conditions are not indicated to be met at 515, such an indication may be stored at the controller such that the engine system diagnostic may be triggered to be conducted responsive to conditions being met for conducting the engine system diagnostic. In a further example where one of the conditions not being indicated to be met at 515 includes the absence of appropriate baseline comparator data (e.g. baseline comparator data obtained greater than the threshold duration prior to execution of the engine system diagnostic, or conditions where the intake air filter (e.g. 215) was replaced or the GPF was regenerated subsequent to obtaining baseline comparator data), the method may include setting flag at the controller and illuminating a malfunction indicator light on a vehicle dash. Such an indication may alert the vehicle operator of a need to service the vehicle, for a potential source of degradation stemming from the intake manifold, exhaust system, or engine compartment, for example, because in the absence of appropriate baseline comparator data, the engine system diagnostic may not be conducted.

To prevent such a situation, in some examples, the vehicle controller may prevent GPF regeneration until an engine system diagnostic has been conducted, responsive to obtaining baseline comparator data. However, the controller may rely on pressure measurements as indicated via the differential pressure sensor (e.g. 263) to determine whether it is important to regenerate the GPF at the expense of an engine system diagnostic, or whether the GPF regeneration may be prevented until the engine system diagnostic has been conducted. For example, if, during engine operation, a threshold pressure differential is obtained via the differential pressure sensor (e.g. 263) corresponding to the GPF, then it may be determined that the GPF may be regenerated, even though such an event may result in the engine system diagnostic not being able to be conducted until subsequent baseline comparator data is obtained.

In a case where the GPF is regenerated subsequent to obtaining baseline comparator data, such that new baseline comparator data may be obtained, a flag may be set at the controller indicating that the GPF was regenerated subsequent to baseline comparator data being obtained, such that new baseline comparator data may be obtained at the next available opportunity (e.g. when conditions are met for obtaining baseline comparator data, as discussed above).

A similar situation may arise if the intake air filter (e.g. 215) is replaced subsequent to baseline comparator data being obtained. For example, a flag may be set at the controller under such circumstances, instructing the vehicle controller to subsequently obtain baseline comparator data at the next opportunity where conditions are indicated to be met for obtaining baseline comparator data.

Returning to step 515 of method 500, if conditions are indicated to be met for conducting the engine system diagnostic, method 500 may proceed to 525, and may include conducting the engine system diagnostic according to FIG. 6. It may be understood that both obtaining baseline comparator data and conducting the engine system diagnostic may comprise substantially equivalent methodology, encompassed by method 600.

Turning now to FIG. 6, a high level example method 600 for obtaining baseline comparator data and/or conducting a portion of the engine system diagnostic, is shown. More specifically, method 600 may be utilized to obtain baseline comparator data that may be used in conjunction with method 500 depicted at FIG. 5, in order to conduct an engine system diagnostic, relying on the baseline comparator data. In this way, a source of degradation may be pinpointed as to stemming from an intake manifold, an exhaust system, or an engine of a vehicle.

Method 600 will be described with reference to the systems described herein and shown in FIGS. 1-4, though it should be understood that similar methods may be applied to other systems without departing from the scope of this disclosure. Method 600 may be carried out by a controller, such as controller 212 in FIG. 2, and may be stored at the controller as executable instructions in non-transitory memory. Instructions for carrying out method 600 and the rest of the methods included herein may be executed by the controller based on instructions stored on a memory of the controller and in conjunction with signals received from sensors of the engine system, such as the sensors described above with reference to FIGS. 1-4. The controller may employ engine system actuators, such as motor (e.g. 120), throttle (e.g. 262), canister purge valve (e.g. 261), etc., according to the method below.

Method 600 begins at 605 and may include controlling a throttle (e.g. 262) to a predetermined throttle position. As discussed above, such a throttle may comprise an electronic throttle, which may be actuated to open or close via the vehicle controller, using power supplied from an onboard energy storage device (e.g. 150), which may include a battery, for example. The predetermined throttle position may comprise a position that is more open than a closed position, for example, to allow intake air to be drawn into the engine via the intake manifold.

Responsive to controlling the throttle to the predetermined throttle position, method 600 may proceed to 610. At 610, method 600 may include rotating the engine unfueled for a predetermined duration at a predetermined speed (e.g. predetermined RPM). Rotating the engine unfueled may comprise rotating the engine in the same direction as when the engine is operated to combust air and fuel. Rotating the engine unfueled may further comprise rotating the engine via the motor (e.g. 120), where the motor may be powered via the onboard energy storage device (e.g. 150), such as a battery. The speed of the engine may be further controlled via the motor, to the predetermined speed. The predetermined engine speed may comprise a speed at which robust measurements of air flow may be obtained via a MAF sensor (e.g. 210), and via a differential pressure sensor (e.g. 263) corresponding to a GPF (e.g. 217). Furthermore, while not explicitly illustrated, it may be understood that a canister purge valve (e.g. 261) may be maintained closed during the spinning the engine, in order to ensure that air is not drawn from the evaporative emissions system and/or fuel system. Still further, while not explicitly shown, for vehicles equipped with exhaust gas recirculation (EGR) (e.g. high pressure EGR and/or low pressure EGR), one or more valve(s) controlling exhaust gas recirculation may be commanded or maintained closed. Even further, for rotating the engine unfueled, valve timing may be controlled to default values.

With the engine being spun unfueled at the predetermined engine speed, method 600 may proceed to 615. At 615, method 600 may include obtaining intake air flow and exhaust flow measurements. More specifically, the MAF sensor (e.g. 210) may be used at step 620 to obtain intake air flow measurements, while the differential pressure sensor (e.g. 263) may be used at step 625 to obtain exhaust flow measurements. Such measurements may be obtained by taking one or more individual measurements over the predetermined duration that the engine is being spun unfueled. In an example where more than one measurement is obtained while the engine is being spun unfueled, such measurements may be averaged or otherwise processed to obtain a high confidence value for the desired measurements.

Such obtained measurements may be stored at the vehicle controller, for use in conducting the engine system diagnostic, discussed in further detail at FIG. 5.

Responsive to the intake and exhaust flow measurements being obtained at step 620 and 625, respectively, method 600 may proceed to 630. At 630, method 600 may include stopping spinning the engine unfueled, and may further comprise returning the throttle to a default configuration. For example, the motor (e.g. 120) may be commanded to bring the engine to a stop, while the vehicle controller may send a signal to the electronic throttle, actuating the throttle to a default position.

As mentioned above, it may be understood that the methodology discussed at FIG. 6 pertains to both obtaining the baseline comparator data, as well as to conducting the engine system diagnostic subsequent to obtaining the baseline comparator data. As such, the methodology will not be discussed again here for brevity. Thus, it may be understood that method 600 may be used in conjunction with FIG. 5 to obtain baseline comparator data at step 510, as well as to conduct the engine system diagnostic at step 525.

Accordingly, returning to step 515 of method 500, responsive to an indication that baseline comparator data has been obtained, and that conditions are met for conducting an engine system diagnostic, method 500 may proceed to 525 where the intake flow and exhaust flow measurements are obtained according to FIG. 6. Responsive to such measurements being obtained, method 500 may proceed to 530. At step 530, method 500 may include interpreting the results of the engine system diagnostic conducted at step 525, according to FIG. 7.

Thus, proceeding to FIG. 7, it illustrates an example lookup table that may be utilized to interpret the results of the engine system diagnostic. Such a lookup table may be stored at the vehicle controller, for example. As illustrated at FIG. 7, there may be four distinct outcomes (A-D) that may result from the engine system diagnostic.

Outcome A may include a situation where the measurement of intake air flow as measured by the MAF sensor is substantially equivalent to the baseline measurement of intake air flow as measured by the MAF sensor, but where exhaust flow as monitored by the differential pressure sensor is greater than the baseline measurement of exhaust flow as measured by the differential pressure sensor. In such an example, it may be indicated that there is a source of degradation stemming from the intake manifold, such as that depicted above at FIG. 3A. As discussed, a source of degradation stemming from the intake manifold may thus result in unmetered air being introduced into the engine, and as such, an exhaust flow may be greater than that expected under conditions where no sources of degradation are present (e.g. under baseline conditions).

Outcome B may include a situation where the measurement of intake air flow as measured by the MAF sensor is substantially equivalent to the baseline measurement of intake air flow as measured by the MAF sensor, but where exhaust flow as monitored by the differential pressure sensor is less than the baseline measurement of exhaust flow as measured by the differential pressure sensor. In such an example, it may be indicated that there is a source of degradation stemming from the exhaust system, such as that depicted above at FIG. 3B. As discussed, a source of degradation stemming from the exhaust system may thus result in exhaust flow being forced to atmosphere via the source of degradation, prior to reaching the differential pressure sensor. Accordingly, such a process may result in a differential pressure sensor reading below that expected under conditions where no sources of degradation are present (e.g. under baseline conditions).

Outcome C may include a situation where both the intake air flow as measured by the MAF sensor, as well the exhaust flow as measured by the differential pressure sensor is less than baseline measurements made by the MAF sensor and the differential pressure sensor. In such an example, it may be understood that there may be a source of degradation stemming from the engine compartment related to engine operation. As discussed, such a source of degradation may comprise intake and/or exhaust valves that are not sealing properly, compression issues related to engine cylinder(s), degraded piston rings, degraded head gasket, undesired camshaft timing, etc. In such a case where the engine is identified as the source of degradation, the engine may not pump as expected, thus resulting in overall less air drawn into the engine via the intake manifold, and a corresponding lower amount of exhaust flow routed through the exhaust system.

Outcome D may include a situation where both the intake air flow as measured by the MAF sensor, as well as the exhaust flow as measured by the differential pressure sensor are substantially equivalent to baseline measurements made by the MAF sensor and the differential pressure sensor. In such an example, an absence of a source of degradation stemming from the intake manifold, exhaust system, and/or engine may be indicated.

It may be understood that in each of the above-discussed potential outcomes A-D, sensor readings that are substantially equivalent to their respective baseline measurements may comprise measurements being within a certain range of each other, for example less than or equal to a 5% difference in measurements over the span of the engine system diagnostic.

Subsequent to interpreting the results of the engine system diagnostic at step 530 of method 500, method 500 may proceed to 535. At 535, method 500 may include adjusting vehicle operating parameters according to the results of the engine system diagnostic. As examples, provided that a source of degradation is identified in the intake manifold, exhaust system, and/or engine, a MIL may be illuminated on the vehicle dash alerting the vehicle operator of the need to service the vehicle.

If a source of degradation is indicated as stemming from the intake manifold, the vehicle controller may adjust throttle position in some examples during fueled engine operation, in order to account for the unmetered air entering the engine via the source of degradation.

In other examples, where the source of degradation is indicated as stemming from either the intake manifold, exhaust system, or engine compartment, adjusting vehicle operating parameters may include the vehicle controller commanding an electric mode of operation as frequently as possible, to mitigate a potential release of undesired emissions to atmosphere, and/or to mitigate potential mechanical issues with the engine under circumstances where the engine is ingesting a greater amount of air than desired, or to mitigate issues already present in the engine compartment.

Turning now to FIG. 8, an example timeline 800 is shown for obtaining baseline comparator measurements as well as conducting an engine system diagnostic according to the methods depicted herein and with reference to FIGS. 5-6, and as applied to the systems depicted herein and with reference to FIGS. 1-4. Timeline 800 includes plot 805, indicating whether an engine is on or off, plot 810, indicating fuel injection status (on or off) to an engine, and plot 815, indicating a position of a throttle (e.g. 262), over time. The throttle may be open, closed, or somewhere in between.

Timeline 800 further includes plot 820, indicating an engine speed (RPM), over time. Engine speed may be 0 (e.g. stopped), or greater than stopped (+). Timeline 800 further includes plot 825, indicating air flow as monitored by a MAF sensor (e.g. 210), and plot 830, indicating exhaust flow as measured by a GFP differential pressure (dP) sensor (e.g. 263), over time. In both plots 825 and 830, sensors may not register any flow (0), or may register flow above 0 (+). Timeline 800 further includes plot 835, indicating an air-fuel ratio, as monitored via an exhaust gas sensor (e.g. 237), over time. Air-fuel ratio may be either stoichiometric (ideal ratio of air to fuel that burns all fuel with no excess air), or may be either rich or lean of stoichiometry.

Timeline 800 further includes plot 840, indicating whether conditions are indicated to be met for obtaining baseline comparator data, plot 845, indicating whether conditions are indicated to be met for conducting an engine system diagnostic, plot 850, indicating whether the vehicle is occupied, and plot 855, indicating whether a source of degradation is present in the engine system, over time. The source may be the engine, intake manifold (intake) or exhaust system (exhaust).

At time t0, the engine is off, and accordingly, fuel is not being injected into engine cylinders, and engine speed is 0 RPM. While not explicitly shown, it may be understood that at time t0, the vehicle is also not being propelled via a motor. A position of a throttle is substantially closed, reflecting a position of the throttle in an engine off/vehicle off state. With the engine off, there is no air-fuel ratio to measure, and thus an air-fuel ratio is not indicated at time t0. Similarly, a MAF sensor positioned in an intake manifold downstream of the throttle is not registering any air flow, and a GPF differential pressure sensor is also not registering any exhaust flow. At time t0, conditions are not indicated to be met for obtaining baseline comparator data, and conditions are further not indicated to be met for conducting an engine system diagnostic test. The vehicle is not indicated to be occupied, and degradation is not indicated in the engine system.

At time t1, conditions are indicated to be met for obtaining baseline comparator data, as discussed above with regard to step 505 of method 500. In this example timeline 800, it may be understood that conditions being met may include a situation where a predetermined duration of time has elapsed since a key-off event, where the controller is woken up in order to obtain the baseline comparator data. In other examples, conditions may be met in response to a remote start event where the vehicle is not occupied, or a situation where the vehicle comprises an autonomous vehicle that is not occupied.

Accordingly, at time t1, responsive to conditions being indicated to be met for obtaining baseline comparator data, the engine is controlled to be spun without fuel injection, where the engine being spun unfueled may comprise spinning the engine via a motor (e.g. 120), powered via an onboard energy storage device (e.g. 150), such as a battery, as discussed above with regard to step 610 of method 600. The motor may control engine speed to a predetermined engine speed, illustrated by plot 820. Furthermore, at time t1, a position of the throttle is controlled to a predetermined throttle position, as discussed above with regard to step 605 of method 600.

Between time t1 and t2, with the engine spinning unfueled, air-fuel ratio, as indicated by an exhaust gas sensor, is indicated to be lean, due to the absence of fuel injection. Intake air flow is monitored between time t1 and t2 by the MAF sensor, and exhaust flow is monitored between time t1 and t2 by the GPF differential pressure sensor. As discussed, such measurements may be stored at the controller of the vehicle, such that subsequent measurements of intake air flow and exhaust flow may be compared to the baseline measurements, in order to pinpoint potential sources of degradation stemming from an intake manifold, exhaust system, or engine of the vehicle.

Subsequent to a predetermined time duration elapsing at time t2, the engine is controlled via the electric motor to 0 RPM. In other words, the engine is spun to rest. While not explicitly illustrated, it may be understood that in the case of a remote start event, subsequent to obtaining baseline comparator data (or subsequent to conducting the engine system diagnostic), rather than spinning the engine to rest, the engine may instead be fueled in anticipation of the vehicle operator operating the vehicle. Furthermore, throttle position is controlled to a default configuration, which in this example includes a configuration that the throttle was at prior to obtaining the baseline comparator data. With the engine being spun to rest, air flow decreases to no flow as measured by the MAF sensor, and exhaust flow decreases to no flow as measured by the GPF differential pressure sensor. As baseline comparator data has been obtained, and stored at the controller, and with the predetermined time duration elapsing at time t2, conditions are no longer indicated to be met for obtaining baseline comparator data.

At time t3, the vehicle becomes occupied. Such an indication may be provided via door sensors, seat load cells, onboard camera(s), etc. At time t4, the engine is turned on, with fuel injection provided to one or more engine cylinders. In other words, by time t4, a vehicle operator has entered the vehicle and started the engine, with the intent to drive the vehicle.

Between time t4 and t5, the vehicle is driven, and accordingly throttle position varies as a function of driver demand, and engine speed is controlled as a function of driver demand. With the engine in operation, both the MAF sensor and the GPF differential pressure sensor measure intake air flow, and exhaust flow, respectively, which varies as a function of driver demand.

Between time t4 and t5, air-fuel ratio is maintained substantially equivalent to stoichiometric air-fuel ratio. However, at time t5, the air-fuel ratio suddenly switches lean. As discussed above, a sudden or abrupt change in air-fuel ratio may be indicative of potential degradation in the engine system. Thus, it may be understood that, in response to the change in air-fuel ratio initiated at time t5, such a result may be stored at the vehicle controller, such that an engine system diagnostic may be initiated at the next opportunity where conditions are indicated to be met for conducting the engine system diagnostic.

Between time t5 and t6, the vehicle is continued to be operated with the engine combusting air and fuel. In some examples, responsive to a disturbance in air-fuel ratio, adaptive fuel learning may correct the lean air-fuel ratio, indicated by dashed line 836. However, in other examples, the vehicle may not include adaptive fuel learning, and as such, may not correct the lean air fuel ratio.

At time t6, the engine is turned off, and fueling to the engine is stopped. At time t7, the vehicle once again becomes unoccupied.

Some time later, at time t8, conditions are indicated to be met for conducting the engine system diagnostic as discussed above with regard to step 515 of method 500. With conditions indicated to be met for the engine system diagnostic, the engine is again spun or rotated via the motor, in the absence of fuel injection. The throttle is controlled to the same predetermined throttle position as the throttle position during obtaining the baseline comparator data. Furthermore, engine speed (RPM) is controlled to the same engine speed as engine speed during obtaining the baseline comparator data.

Accordingly, between time t8 and t9, MAF sensor readings are obtained, in addition to GPF differential pressure sensor readings. With the engine spinning unfueled, the air-fuel ratio is indicated to be lean during the engine spinning. Line 826 indicates a baseline MAF sensor measurement, obtained between time t1 and t2. Similarly, line 831 indicates a baseline GPF differential pressure sensor measurement, obtained between time t1 and t2.

At time t9, the engine system diagnostic is complete, as a predetermined time duration has elapsed (the predetermined time duration substantially equivalent to the predetermined time duration of engine spinning for obtaining baseline comparator data). With the engine system diagnostic complete, the vehicle controller may compare values obtained from the MAF sensor and GPF differential pressure sensor during the engine system diagnostic, to the respective values obtained during the obtaining of baseline comparator data. As discussed above, a lookup table, such as lookup table 700 depicted above at FIG. 7, may be utilized to interpret the results of the engine system diagnostic. In this example timeline, MAF sensor readings during the engine system diagnostic are indicated to be substantially equivalent to respective MAF sensor readings obtained during the obtaining of baseline comparator data. Furthermore, GPF differential pressure sensor readings during the engine system diagnostic are indicated to be greater than the respective GPF differential pressure sensor readings obtained during the obtaining of baseline comparator data. Such an example thus represents outcome A as discussed above with regard to FIG. 7, where degradation stemming from the intake manifold is indicated.

In this way, degradation stemming from one of an intake manifold, exhaust system (upstream of GPF differential pressure sensor and downstream of the engine), or engine of an engine system may be pinpointed by making use of intake air flow measurements and exhaust flow measurements, in comparison to baseline intake air flow and exhaust flow measurements, where the baseline intake air flow and exhaust flow measurements are obtained under conditions where the engine system is free from degradation. By pinpointing the source of degradation, customer satisfaction may be improved, as time spent working on the vehicle via a technician may be reduced.

The technical effect is to recognize that a mass air flow sensor positioned in the intake manifold of an engine is not able to effectively diagnose a source of degradation stemming from the intake manifold, unless such a measurement of mass air flow is considered in conjunction with a pressure sensor in the exhaust system. Similarly, a source of degradation stemming from an engine, or exhaust system are not directly inferable unless measurements of intake air flow and exhaust flow are considered together. In all examples (e.g. source of degradation stemming from the intake manifold, exhaust system, or engine), a further technical effect is to recognize that measurements of intake air flow and exhaust flow may be compared to baseline measurements of intake air flow and exhaust flow, such that by comparing both intake air flow and exhaust flow to baseline intake air flow and exhaust flow measurements, respectively, may enable a determination of a source of degradation. A still further technical effect is to recognize that conditions for baseline measurements and for measurements of intake air flow and exhaust flow during an actual test diagnostic may be substantially equivalent by rotating the engine unfueled for a predetermined duration, at a predetermined engine speed and with a throttle controlled to a predetermined opened position. In this way, a source of degradation stemming from the intake manifold, exhaust system, or engine may be conclusively diagnosed.

The systems described herein, and with reference to FIGS. 1-4, along with the methods described herein, and with reference to FIGS. 5-6, may enable one or more systems and one or more methods. In one example, a method comprises conducting an engine system diagnostic by rotating an engine of a vehicle unfueled to draw an intake air flow into the engine via an intake manifold and to route an exhaust flow via an exhaust system to atmosphere; and indicating a source of degradation stemming from one of the engine, the intake manifold, or the exhaust system based on both the intake air flow and the exhaust flow during the rotating. In a first example of the method, the method further comprises prior to conducting the engine system diagnostic, obtaining a set of baseline comparator data that includes a baseline intake air flow and a baseline exhaust flow under a substantially equivalent set of conditions as that for conducting the engine system diagnostic, including rotating the engine unfueled via a motor powered via a battery. A second example of the method optionally includes the first example, and further includes wherein the substantially equivalent set of conditions further comprises rotating the engine at a predetermined speed for a predetermined duration of time, and controlling a throttle positioned in the intake manifold to a predetermined position to allow air to be drawn into the engine via the intake manifold. A third example of the method optionally includes any one or more or each of the first through second examples, and further includes wherein the intake air flow and the baseline intake air flow is measured via a mass air flow sensor positioned in the intake manifold, and wherein the exhaust flow and the baseline exhaust flow is measured via a pressure sensor positioned in the exhaust system. A fourth example of the method optionally includes any one or more or each of the first through third examples, and further includes wherein the pressure sensor comprises a differential pressure sensor corresponding to a gas particulate filter positioned in the exhaust system. A fifth example of the method optionally includes any one or more or each of the first through fourth examples, and further includes wherein obtaining the set of baseline comparator data is conducted under conditions where the engine system is free from the source of degradation. A sixth example of the method optionally includes any one or more or each of the first through fifth examples, and further includes wherein the source of degradation is indicated in the intake manifold responsive to the intake air flow during the engine system diagnostic being substantially equivalent to the baseline intake flow, but wherein the exhaust flow during the engine system diagnostic is greater than the baseline exhaust flow. A seventh example of the method optionally includes any one or more or each of the first through sixth examples, and further includes wherein the source of degradation is indicated in the exhaust system responsive to the intake air flow during the engine system diagnostic being substantially equivalent to the baseline intake air flow, but wherein the exhaust flow is lower during the engine system diagnostic as compared to the baseline exhaust flow. An eighth example of the method optionally includes any one or more or each of the first through seventh examples, and further includes wherein the source of degradation is indicated as stemming from the engine responsive to both the intake air flow and the exhaust flow during the engine system diagnostic being lower than the baseline intake air flow and the baseline exhaust flow, respectively. A ninth example of the method optionally includes any one or more or each of the first through eighth examples, and further includes wherein the source of degradation is not present in any of the intake manifold, exhaust system, or engine responsive to both the intake air flow during the engine system diagnostic being substantially equivalent to the baseline intake air flow, and the exhaust flow during the engine system diagnostic being substantially equivalent to the baseline exhaust flow.

An example of a system for a vehicle comprises an engine system including an intake manifold, an exhaust system, and an engine; a mass air flow sensor positioned in the intake manifold; a differential pressure sensor positioned in the exhaust system, configured to measure a pressure difference across a gasoline particulate filter positioned in the exhaust system; a motor, capable of rotating the engine; and a controller, storing instructions in non-transitory memory that, when executed, cause the controller to: in a first condition, obtain a set of baseline measurements of intake air flow and exhaust flow via the mass air flow sensor and the differential pressure sensor, respectively; in a second condition, obtain a set of test measurements of intake air flow and exhaust flow during conducting an engine system diagnostic, which includes indicating a presence or absence of a degradation source stemming from one of the intake manifold, the exhaust system, or the engine; and wherein the presence or absence of the degradation source is based on comparing both 1) the baseline measurements of intake air flow and the test measurements of intake air flow obtained during both the first and second conditions, respectively, to one another, and 2) the baseline measurements of exhaust flow and the test measurements of exhaust flow obtained during both the first and second conditions, respectively, to one another. In a first example of the system, the system further comprises additional instructions to: indicate the presence of the degradation source in the intake manifold responsive to the test measurements of intake air flow being substantially equivalent to the baseline measurements of intake flow, but where the test measurements of exhaust flow are greater than the baseline measurements of exhaust flow; indicate the presence of the degradation source in the exhaust system responsive to the test measurements of intake air flow being substantially equivalent to the baseline measurements of intake air flow, but where the test measurements of exhaust flow is lower than the baseline measurements of exhaust flow; and indicate the presence of the degradation source in the engine responsive to both the test measurements of intake air flow being lower than the baseline measurements of intake air flow, and the test measurements of exhaust flow being lower than the baseline measurements of exhaust flow. A second example of the system optionally includes the first example, and further comprises a throttle positioned in the intake manifold; and wherein the controller stores further instructions to, in both the first and second conditions, rotate the engine unfueled via the motor, for a predetermined duration, with the throttle controlled to a predetermined position to allow air to be drawn into the engine while the engine is being rotated unfueled. A third example of the system optionally includes any one or more or each of the first and second examples, and further comprises an intake air filter positioned upstream of the throttle, and wherein the controller stores additional instructions to: obtain the set of test measurements of intake air flow and exhaust flow in the second condition responsive to an indication that the set of baseline measurements of intake air flow and exhaust flow have been obtained in the first condition, and further responsive to an indication that the gasoline particulate filter has not been regenerated and that the intake air filter has not been replaced since obtaining the set of baseline measurements of intake air flow and exhaust flow in the first condition. A fourth example of the system optionally includes any one or more or each of the first through third examples, and further comprises additional instructions to: obtain the set of test measurements of intake air flow and exhaust flow and obtain the set of baseline measurements of intake air flow and exhaust flow responsive to an indication that the vehicle is not occupied in both the first and second conditions. A fifth example of the system optionally includes any one or more or each of the first through fourth examples, and further comprises additional instructions to prevent regeneration of the gasoline particulate filter responsive to obtaining the set of baseline measurements of intake air flow and exhaust flow in the first condition, provided that a pressure difference across the gasoline particulate filter is not above a threshold pressure difference. A sixth example of the system optionally includes any one or more or each of the first through fifth examples, and further comprises additional instructions to again obtain the set of baseline measurements of intake air flow and exhaust flow prior to the second condition, responsive to the gasoline particulate filter being regenerated subsequent to the first condition and prior to the second condition.

Another example of a method comprises rotating an engine of a vehicle unfueled to draw air into the engine via an intake manifold and then exhaust the air to atmosphere via an exhaust system, in order to obtain a set of baseline measurements of intake air flow and exhaust flow, where the set of baseline measurements of intake air flow and exhaust flow are subsequently compared to a set of test measurements of intake air flow and exhaust flow under a set of conditions substantially equivalent to those for obtaining the set of baseline measurements of intake air flow and exhaust flow; and indicating a presence or absence of a source of degradation stemming from one of the intake manifold, the exhaust system, or the engine based on the comparing the set of baseline measurements of intake air flow and exhaust flow to the set of test measurements of intake air flow and exhaust flow. In a first example of the method, the method further comprises indicating the absence of the source of degradation in the intake manifold, the exhaust system, and the engine responsive to the set of test measurements of intake air flow and exhaust flow both being substantially equivalent to the set of baseline measurements of intake air flow and exhaust flow, respectively; indicating the presence of the source of degradation in the intake manifold responsive to the test measurements of intake air flow being substantially equivalent to the baseline measurements of intake air flow, but where the test measurements of exhaust flow are greater than the baseline measurements of exhaust flow; indicating the presence of the source of degradation in the exhaust system responsive to the test measurements of intake air flow being substantially equivalent to the baseline measurements of intake air flow, but where the test measurements of exhaust flow are less than the baseline measurements of exhaust flow; and indicating the presence of the source of degradation stemming from the engine responsive to the test measurements of intake air flow being lower than the baseline measurements of intake air flow, and the test measurements of exhaust flow being lower than the baseline measurements of exhaust flow. A second example of the method optionally includes the first example, and further includes wherein the rotating the engine unfueled is conducted under conditions where the vehicle is not-occupied and the vehicle is not in motion; and wherein the set of conditions substantially equivalent for obtaining the set of test measurements of intake air flow and exhaust flow and the set of baseline measurements of intake air flow and exhaust flow include rotating the engine at a predetermined speed for a predetermined duration, with a throttle positioned in an engine intake controlled to a predetermined position, and further responsive to an indication that a filter positioned upstream of the throttle, or a particulate filter positioned in the exhaust system, have not been replaced or regenerated, respectively, subsequent to obtaining the set of baseline measurements of intake air flow and exhaust flow.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method comprising:
   conducting an engine system diagnostic on an engine system by rotating an engine of a vehicle unfueled to draw an intake air flow into the engine via an intake manifold and to route an exhaust flow via an exhaust system to atmosphere; and
   indicating a source of degradation stemming from one of the engine, the intake manifold, or the exhaust system based on both the intake air flow and the exhaust flow during the rotating.

2. The method of claim 1, further comprising:
   prior to conducting the engine system diagnostic, obtaining a set of baseline comparator data that includes a baseline intake air flow and a baseline exhaust flow under a substantially equivalent set of conditions as that for conducting the engine system diagnostic, including rotating the engine unfueled via a motor powered via a battery.

3. The method of claim 2, wherein the substantially equivalent set of conditions further comprises rotating the engine at a predetermined speed for a predetermined duration of time, and controlling a throttle positioned in the intake manifold to a predetermined position to allow air to be drawn into the engine via the intake manifold.

4. The method of claim 2, wherein the intake air flow and the baseline intake air flow is measured via a mass air flow sensor positioned in the intake manifold, and wherein the exhaust flow and the baseline exhaust flow is measured via a pressure sensor positioned in the exhaust system.

5. The method of claim 4, wherein the pressure sensor comprises a differential pressure sensor corresponding to a gas particulate filter positioned in the exhaust system.

6. The method of claim 2, wherein obtaining the set of baseline comparator data is conducted under conditions where the engine system is free from the source of degradation.

7. The method of claim 2, wherein the source of degradation is indicated in the intake manifold responsive to the intake air flow during the engine system diagnostic being substantially equivalent to the baseline intake flow, but wherein the exhaust flow during the engine system diagnostic is greater than the baseline exhaust flow.

8. The method of claim 2, wherein the source of degradation is indicated in the exhaust system responsive to the intake air flow during the engine system diagnostic being substantially equivalent to the baseline intake air flow, but wherein the exhaust flow is lower during the engine system diagnostic as compared to the baseline exhaust flow.

9. The method of claim 2, wherein the source of degradation is indicated as stemming from the engine responsive to both the intake air flow and the exhaust flow during the engine system diagnostic being lower than the baseline intake air flow and the baseline exhaust flow, respectively.

10. The method of claim 2, wherein the source of degradation is not present in any of the intake manifold, the exhaust system, or the engine responsive to both the intake air flow during the engine system diagnostic being substantially equivalent to the baseline intake air flow, and the exhaust flow during the engine system diagnostic being substantially equivalent to the baseline exhaust flow.

11. A system for a vehicle, comprising:
   an engine system including an intake manifold, an exhaust system, and an engine;
   a mass air flow sensor positioned in the intake manifold;
   a differential pressure sensor positioned in the exhaust system, configured to measure a pressure difference across a gasoline particulate filter positioned in the exhaust system;
   a motor, capable of rotating the engine;
   a throttle positioned in the intake manifold; and
   a controller, storing instructions in non-transitory memory that, when executed, cause the controller to: in a first condition, obtain a set of baseline measurements of intake air flow and exhaust flow via the mass air flow sensor and the differential pressure sensor, respectively; in a second condition, obtain a set of test measurements of intake air flow and exhaust flow during conducting an engine system diagnostic, which includes indicating a presence or absence of a degradation source stemming from one of the intake manifold, the exhaust system, or the engine; and wherein the presence or absence of the degradation source is based on comparing both 1) the baseline measurements of intake air flow and the test measurements of intake air flow obtained during both the first and second conditions, respectively, to one another, and 2) the baseline measurements of exhaust flow and the test measurements of exhaust flow obtained during both the first and second conditions, respectively, to one another; and wherein the controller stores further instructions to in both the first and second conditions, rotate the engine unfueled via the motor, for a predetermined duration, with the throttle controlled to a predetermined position to allow air to be drawn into the engine while the engine is being rotated unfueled.

12. The system of claim 11, further comprising additional instructions to:
   indicate the presence of the degradation source in the intake manifold responsive to the test measurements of intake air flow being substantially equivalent to the baseline measurements of intake flow, but where the test measurements of exhaust flow are greater than the baseline measurements of exhaust flow;
   indicate the presence of the degradation source in the exhaust system responsive to the test measurements of intake air flow being substantially equivalent to the baseline measurements of intake air flow, but where the test measurements of exhaust flow are lower than the baseline measurements of exhaust flow; and indicate the presence of the degradation source in the engine responsive to both the test measurements of intake air flow being lower than the baseline measurements of intake air flow, and the test measurements of exhaust flow being lower than the baseline measurements of exhaust flow.

13. The system of claim 11, further comprising an intake air filter positioned upstream of the throttle, and wherein the controller stores additional instructions to:

obtain the set of test measurements of intake air flow and exhaust flow in the second condition responsive to an indication that the set of baseline measurements of intake air flow and exhaust flow have been obtained in the first condition, and further responsive to an indication that the gasoline particulate filter has not been regenerated and that the intake air filter has not been replaced since obtaining the set of baseline measurements of intake air flow and exhaust flow in the first condition.

14. The system of claim 11, further comprising additional instructions to:

obtain the set of test measurements of intake air flow and exhaust flow and obtain the set of baseline measurements of intake air flow and exhaust flow responsive to an indication that the vehicle is not occupied in both the first and second conditions.

15. The system of claim 11, further comprising additional instructions to prevent regeneration of the gasoline particulate filter responsive to obtaining the set of baseline measurements of intake air flow and exhaust flow in the first condition, provided that the pressure difference across the gasoline particulate filter is not above a threshold pressure difference.

16. The system of claim 11, further comprising additional instructions to again obtain the set of baseline measurements of intake air flow and exhaust flow prior to the second condition, responsive to the gasoline particulate filter being regenerated subsequent to the first condition and prior to the second condition.

17. A method comprising:

rotating an engine of a vehicle unfueled to draw air into the engine via an intake manifold and then exhaust the air to atmosphere via an exhaust system, in order to obtain a set of baseline measurements of intake air flow and exhaust flow, where the set of baseline measurements of intake air flow and exhaust flow are subsequently compared to a set of test measurements of intake air flow and exhaust flow under a set of conditions substantially equivalent to those for obtaining the set of baseline measurements of intake air flow and exhaust flow; and indicating a presence or absence of a source of degradation stemming from one of the intake manifold, the exhaust system, or the engine based on the comparing the set of baseline measurements of intake air flow and exhaust flow to the set of test measurements of intake air flow and exhaust flow.

18. The method of claim 17, further comprising:

indicating the absence of the source of degradation in the intake manifold, the exhaust system, and the engine responsive to the set of test measurements of intake air flow and exhaust flow both being substantially equivalent to the set of baseline measurements of intake air flow and exhaust flow, respectively;

indicating the presence of the source of degradation in the intake manifold responsive to the test measurements of intake air flow being substantially equivalent to the baseline measurements of intake air flow, but where the test measurements of exhaust flow are greater than the baseline measurements of exhaust flow;

indicating the presence of the source of degradation in the exhaust system responsive to the test measurements of intake air flow being substantially equivalent to the baseline measurements of intake air flow, but where the test measurements of exhaust flow are less than the baseline measurements of exhaust flow; and indicating the presence of the source of degradation stemming from the engine responsive to the test measurements of intake air flow being lower than the baseline measurements of intake air flow, and the test measurements of exhaust flow being lower than the baseline measurements of exhaust flow.

19. The method of claim 17, wherein the rotating the engine unfueled is conducted under conditions where the vehicle is not-occupied and the vehicle is not in motion; and wherein the set of conditions substantially equivalent for obtaining the set of test measurements of intake air flow and exhaust flow and the set of baseline measurements of intake air flow and exhaust flow include rotating the engine at a predetermined speed for a predetermined duration, with a throttle positioned in an engine intake controlled to a predetermined position, and further responsive to an indication that a filter positioned upstream of the throttle, or a particulate filter positioned in the exhaust system, have not been replaced or regenerated, respectively, subsequent to obtaining the set of baseline measurements of intake air flow and exhaust flow.

* * * * *